(12) United States Patent
Shankar et al.

(10) Patent No.: US 7,642,272 B2
(45) Date of Patent: Jan. 5, 2010

(54) CANNABINOID RECEPTOR LIGANDS

(75) Inventors: Bandarpalle B. Shankar, Branchburg, NJ (US); Razia K. Rizvi, Bloomfield, NJ (US); Joseph A. Kozlowski, Princeton, NJ (US); Neng-Yang Shih, Warren, NJ (US)

(73) Assignee: Schering Corporation, Kenilworth, NJ (US)

( * ) Notice: Subject to any disclaimer, the term of this patent is extended or adjusted under 35 U.S.C. 154(b) by 164 days.

(21) Appl. No.: 10/803,577

(22) Filed: Mar. 18, 2004

(65) Prior Publication Data
US 2004/0186148 A1 Sep. 23, 2004

Related U.S. Application Data

(60) Provisional application No. 60/456,268, filed on Mar. 20, 2003.

(51) Int. Cl.
C07D 401/02 (2006.01)
A61K 31/44 (2006.01)

(52) U.S. Cl. ............... 514/339; 514/235.5; 514/252.12; 514/421; 514/461; 514/709; 544/124; 544/386; 546/268.1; 546/339; 548/469; 549/429; 568/28

(58) Field of Classification Search .................... 568/28; 514/709
See application file for complete search history.

(56) References Cited

U.S. PATENT DOCUMENTS

| | | | | |
|---|---|---|---|---|
| 3,096,375 | A | * | 7/1963 | Campbell et al. ............. 568/38 |
| 4,466,965 | A | | 8/1984 | Stout et al. |
| 4,567,184 | A | | 1/1986 | Musser et al. |
| 5,332,820 | A | | 7/1994 | Duncia |
| 5,338,753 | A | | 8/1994 | Burstein et al. |
| 5,462,960 | A | | 10/1995 | Barth et al. |
| 5,486,525 | A | | 1/1996 | Summers, Jr. et al. |
| 5,532,237 | A | | 7/1996 | Gallant et al. |
| 5,747,524 | A | | 5/1998 | Cullinan et al. |
| 5,925,768 | A | | 7/1999 | Barth et al. |
| 5,948,777 | A | | 9/1999 | Bender et al. |
| 5,990,170 | A | | 11/1999 | Della Valle et al. |
| 6,013,648 | A | | 1/2000 | Rinaldi et al. |
| 6,017,919 | A | | 1/2000 | Inaba et al. |
| 6,100,259 | A | | 8/2000 | Elliott et al. |

FOREIGN PATENT DOCUMENTS

| | | |
|---|---|---|
| DE | 19533644 | 9/1995 |
| EP | 0181568 | 5/1986 |
| EP | 0401030 | 12/1990 |
| EP | 0407217 | 1/1991 |
| EP | 0885889 | 12/1998 |
| EP | 1031571 | 8/2000 |
| EP | 1283039 | 2/2003 |
| FR | 2839718 | 11/2003 |
| JP | 06072979 | 3/1994 |
| WO | WO 93/21158 | 10/1993 |
| WO | WO 96/23783 | 8/1996 |
| WO | WO 97/03953 | 2/1997 |
| WO | WO 98/10763 | 3/1998 |
| WO | WO 98/31227 | 7/1998 |
| WO | WO 98/33769 | 8/1998 |
| WO | WO 98/41519 | 9/1998 |
| WO | WO 99/26612 | 6/1999 |
| WO | WO 99/36393 | 7/1999 |
| WO | WO 99/50245 | 10/1999 |
| WO | WO 00/06146 | 2/2000 |
| WO | WO 01/28557 A1 | 4/2001 |
| WO | WO 01/29007 | 4/2001 |
| WO | WO 01 32169 | 5/2001 |
| WO | WO 01/37826 | 5/2001 |
| WO | WO 01/44172 | 6/2001 |
| WO | WO 01/44239 | 6/2001 |
| WO | WO 01/64642 | 9/2001 |
| WO | WO 01/70753 | 9/2001 |
| WO | WO 01/74762 | 10/2001 |
| WO | WO 01/83460 | 11/2001 |
| WO | WO 02/42248 | 5/2002 |
| WO | WO 02/060447 | 8/2002 |
| WO | WO 02/062750 | 8/2002 |
| WO | WO 03/020217 | 3/2003 |
| WO | WO 03/042174 | 5/2003 |
| WO | WO 03/091189 A1 | 11/2003 |
| WO | WO 03/097597 A2 | 11/2003 |
| WO | WO 2004/017920 | 3/2004 |
| WO | WO 2004/018433 | 3/2004 |
| WO | WO 2004/029026 | 4/2004 |

(Continued)

OTHER PUBLICATIONS

Truce et al, Journal of the American Chemical Society, vol. 83, pp. 4641-4643, 1961.*

(Continued)

*Primary Examiner*—Zinna N Davis
(74) *Attorney, Agent, or Firm*—Keith D. MacMillan; Thomas A. Blinka; William Y. Lee

(57) ABSTRACT

There are disclosed compounds of the formula I

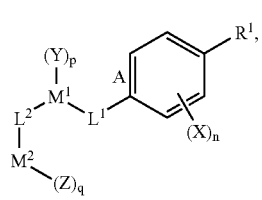

a pharmaceutically acceptable salt or solvate of the compound, which exhibit anti-inflammatory and immunomodulatory activity. Also disclosed are pharmaceutical compositions containing said compounds.

44 Claims, No Drawings

FOREIGN PATENT DOCUMENTS

WO    WO 2004/029027    4/2004

OTHER PUBLICATIONS

Truce et al, Tetrahedron, 1965, vol. 21, pp. 2899-2905.*
Adams et al, Croatica Chemica Acta, 1957, vol. 29, pp. 277-285.*
Mustafa, Journal of the Chemical Society, 1949, pp. 2151-2152.*
M. Curtin et al., "Discovery and Evaluation of a Series of 3-Acylindole Imidazopyridine Platelet-Activating Factor Antagonists", 41(I) *J. Med. Chem.* 74-95 (1998).
G. Hartman et al., "4-Substituted Thiophene—Furan—2-sulfonamides as topical carbonic anhydrase inhibitors" 35(21) *J. Med. Chem.* 3822-31 (1992).
G. Hartman et al., "Synthesis and derivatization of 4-(arylsulfonyl) thiophene—and—furan—2 sulfonamides", 27(2) *J. Heterocycl. Chem.* 127-34 (1990).
P. Cozzi et al., New N-(2-ethoxyethyl)-N-(4-phenoxybenzyl) dichloroacetamides as potent antiamebic agents 18(3) *Eur. J. Med. Chem.* 203-208 (1983).
U.S. Appl. No. 10/214,897, (AL01381K1) for "Cannabinoid Receptor Ligands", filed Aug. 5, 2003.
U.S. Appl. No. 10/464,174, (AL01561K) for "Cannabinoid Receptor Agonists", filed Jun. 17, 2003.
R.G. Pertwee, "Pharmacology of Cannabinoid Receptor Ligands", Curr. Med. Chem 6(8), (1999), 635-664.
T.W. Greene et al. Protective Groups in Organic Synthesis (1981), Wiley, New York.
T. Higuchi and V. Stella, Pro-drugs as Novel Drug Delivery Systems (1975) 14 of the A.C.S. Symposium Series.
Bio reversible Carriers in Drug Design, (1987) Edward B. Roche, ed., American Pharmaceutical Association and Pergamon Press.
S. Berge et al., "Pharmaceutical Salts", Journal of Pharmaceutical Sciences (1977) 66(1) 1-19.
P. Gould, "Salt Selection for Basic Drugs", International J. of Pharmaceutics (1986) 33 201-217.
Anderson et al, The Practice of Medicinal Chemistry (1996), Academic Press, New York.
International Search Report for PCT/US 03/19245 (AL01561K)—5 Pages.
International Search Report for PCT/US 03/24398 dated May 8, 2003 for AL01381K1—6 Pages.
International Search Report for PCT/US2004/008333 dated Jul. 10, 2004 for 12 Pages.
Database Beilstein, Beilstein Institute for Organic Chemistry, Frankfurt—Main, De; XP002294088 retrieved from XFIRE Database accession No. 9568402, 9579279, 9582786, 9563319 Abstract & Biorg, Med. Chem. vol. 11, No. 18, 2003, pp. 3965-3974.
Database Beilstein Beilstein Institute for Organic Chemistry, Frankfurt—Main, De; XP002294089 retrieved from XFIRE Database accession No. 8176641, 8176893 Abstract & Mol. Pharmacol. vol. 48, No. 2, 1995, pp. 352-361.
Database Beilstein, Beilstein Institute for Organic Chemistry, Frankfurt—Main, De; XP002294090 retrieved from XFIRE Database accession No. 8284677, 8286894, 8287610, 8289960, 8290344, 7780291, 7780333, 8288409, 7231571 Abstract & J. Med. Chem. vol. 42, No. 4, 1999, pp. 769-776.
Database Beilstein, Beilstein Institute for Organic Chemistry, Frankfurt—Main, De; XP02294091 retrieved from XFIRE Database accession No. 8360417 Abstract & J. Pharmacol, vol. 126, 1999, pp. 665-672.
Database Beilstein, Beilstein Institute for Organic Chemistry, Frankfurt—Main, De; XP002294092 retrieved from XFIRE Database accession No. 8795090 Abstract & J. Pharmacol, Exp. Ther., vol. 284, No. 1, 1998, pp. 291-297.
Database Beilstein, Beilstein Institute for Organic Chemistry, Frankfurt—Main, De; XP002294093 retrieved from XFIRE Database accession No. 496619 Abstract & Bioorg. Med. Chem. Lett vol. 6 No. 19, 1996, pp. 2263-2268.
Database Beilstein, Beilstein Institute for Organic Chemistry, Frankfurt—Main, De; XP002294094 retrieved from XFIRE Database accession No. 2216071 Abstract & Pharmacol. Toxicol. vol. 80, 1997, pp. 103-107.
Database Beilstein, Beilstein Institute for Organic Chemistry, Frankfurt—Main, De; XP002294095 retrieved from XFIRE Database accession No. 7226937 Abstract & Bioorg. Med. Chem. Lett. vol. 6, No. 1, 1996, pp. 17-22.
Database Beilstein, Beilstein Institute for Organic Chemistry, Frankfurt—Main, De; XP002294096 retrieved from XFIRE Database accession No. 497341 Abstract & Xenobiotica, vol. 24, No. 7, 1994, pp. 603-612.
Database Beilstein, Beilstein Institute for Organic Chemistry, Frankfurt—Main, De; XP002294097 retrieved from XFIRE Database accession No. 7392775, 7389552, 7390283, 7392387 Abstract & J. Mde. Chem. vol. 41, No. 23, 1998, pp. 4521-4532.
Database Beilstein, Beilstein Institute for Organic Chemistry, Frankfurt—Main, De; XP002294098 retrieved from XFIRE Database accession No. 4302866 Abstract & J. Pharm. Pharmacol. vol. 53, No. 11, 2001, pp. 1525-1532.
Database Beilstein, Beilstein Institute for Organic Chemistry, Frankfurt—Main, De; XP002294099 retrieved from XFIRE Database accession No. 1610624 Abstract & Chem. Pharm. Bull., vol. 42, No. 7, 1994, pp. 1459-1462.
Database Beilstein, Beilstein Institute for Organic Chemistry, Frankfurt—Main, De; XP002294100 retrieved from XFIRE Database accession No. 4604978 Abstract & J. Heterocycl. Chem., vol. 19, 1982, pp. 953-956.
Database Beilstein, Beilstein Institute for Organic Chemistry, Frankfurt—Main, De; XP002294101 retrieved from XFIRE Database accession No. 5466453 Abstract & Pharmazie, vol. 47, No. 6, 1992, pp. 409-411.
Database Beilstein, Beilstein Institute for Organic Chemistry, Frankfurt—Main, De; XP002294102 retrieved from XFIRE Database accession No. 19404468 Abstract & Aust. J. Chem vol. 32, 1979, pp. 1531-1550.
Database Beilstein, Beilstein Institute for Organic Chemistry, Frankfurt—Main, De; XP002294142 retrieved from XFIRE Database accession No. 232835 Abstract & J. Org. Chem., vol. 46, No. 20, 1981, pp. 4051-4057.
Bell, Craig H., et al., "The Chemistry of Aryllead(IV) Tricarboxylates. Reaction with Aromatics to Give Biaryls", Aust. J. Chem., (1979) pp. 1531-1550, vol. 32.
D'Ambra, Thomas E., et al., "C-Attached Aminoalkylindoles: Potent Cannabinoid Mimetics", Bioorganic & Medicinal Chemistry Letters, (1996), pp. 17-22, vol. 6, No. 1.
Felder, Christian C., et al., "LY320135, a Novel Cannabinoid CB1 Receptor Antagonist, Unmasks Coupling of the CB1 Receptor to Stimulation of cAMP Accumulation[1]", The Journal of Pharmacology and Experimental Therapeutics, (1998), pp. 291-297, vol. 284, No. 1.
Gallant, Michel, et al., "New Class of Potent Ligands for the Human Peripheral Cannabinoid Receptor", Bioorganic & Medicinal Chemistry Letters, (1996), pp. 2263-2268, vol. 6, No. 19.
Gensler, Walter J., et al., "Reaction Pathway for the Formation of 3,3-Diphenyl-1-benzenesulfonamidopropane in the Aluminum Chloride Catalyst Reaction of 1-Benzenesulfonyl-2-(bromomethyl)ethylenimine and Benzene", J. Org. Chem., (1981), pp. 4051-4057, vol. 46, No. 20.
Lan, Ruoxi, et al., "Structure-Activity Relationships of Pyrazole Derivatives as Cannabinoid Receptor Antagonists", J. Med. Chem., (1999), pp. 769-776, vol. 42.
Osman, A.M., et al., "Synthesis and Some Reactions of Naphth[1,2-*d*]oxazole-5-sulfonic Acids", J. Heterocyclic Chem., (1982), pp. 953-956, vol. 19.
Ross, Ruth A., et al., "Agonist-inverse agonist characterization at $CB_1$ and $CB_2$ cannabinoid receptors of L759633, L759656 and AM630", British Journal of Pharmacology, (1999), pp. 665-672, vol. 126.
Shim, Joong-Youn, et al., "Three-Dimensional Quantitative Structure-Activity Relationship Study of the Cannabimimetic (Aminoalkyl)indoles Using Comparative Molecular Field Analysis", J. Med. Chem., (1998), pp. 4521-4532, vol. 41, No. 23.

English translation of First Office Action (PCT application entering into the national phase) Chinese Patent Application No. 200480007295.X, issued Feb. 2, 2007.

* cited by examiner

US 7,642,272 B2

CANNABINOID RECEPTOR LIGANDS

CROSS-REFERENCE TO RELATED APPLICATION

This application claims the benefit of priority from U.S. Provisional Patent Application Ser. No. 60/456,268, filed Mar. 20, 2003.

BACKGROUND OF THE INVENTION

Field of the Invention

The present invention relates to cannabinoid receptor ligands and, more particularly, to compounds that bind to cannabinoid ($CB_2$) receptors. Compounds according to the present invention generally exhibit anti-inflammatory and immunomodulatory activity and can be useful in treating conditions characterized by inflammation and immunomodulatory irregularities. Examples of conditions which may be treated include, but are not limited to, rheumatoid arthritis, asthma, allergy, psoriasis, Crohn's disease, systemic lupus erythematosus, multiple sclerosis, diabetes, cancer, glaucoma, osteoporosis, renal ischemia, cerebral stroke, cerebral ischemia, and nephritis. The invention also relates to pharmaceutical compositions containing said compounds.

Cannabinoid receptors belong to the superfamily of G-protein coupled receptors. They are classified into the predominantly neuronal $CB_1$ receptors and the predominantly peripheral $CB_2$ receptors. While the effects of $CB_1$ receptors are principally associated with the central nervous system, $CB_2$ receptors are believed to have peripheral effects related to bronchial constriction, immunomodulation and inflammation. As such, a selective $CB_2$ receptor binding agent is expected to have therapeutic utility in the control of diseases associated with inflammation, immunomodulation and bronchial constriction such as rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis (see, e.g., R. G. Pertwee, Curr. Med. Chem. 6(8), (1999), 635).

Various compounds have reportedly been developed which interact with $CB_2$ receptors and/or which have, inter alia, anti-inflammatory activity associated with cannabinoid receptors. See, e.g., U.S. Pat. Nos. 5,338,753, 5,462,960, 5,532,237, 5,925,768, 5,948,777, 5,990,170, 6,013,648 and 6,017,919.

SUMMARY OF THE INVENTION

In its many embodiments, the present invention provides compounds of formula I:

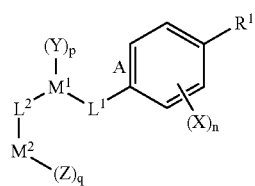

I or a pharmaceutically acceptable salt or solvate thereof, wherein n is 0 to 4;
p is 0 to 4;
q is 0 to 5;

X is selected from the group consisting of hydrogen, alkoxy, alkyl, aryl, cycloalkyl, cycloalkenyl, heterocyclyl, heterocyclenyl, haloalkoxy, haloalkyl, halogen, heteroalkyl, heteroaryl, —$CF_3$, —CN, —C(O)N($R^2$)$_2$, —C(O)O$R^2$, —N($R^2$)$_2$, —NHC(O)$R^2$, —$NR^2$C(O)O$R^2$, —$NR^2$C(O)N($R^2$)$_2$, —$NO_2$, —NC(=N—CN)NH$R^2$, —OCF$_2$H, —OCF$_3$, —OH and —S($O_2$)N($R^2$)$_2$, with the proviso that when n is 2, 3 or 4, the X moieties can be the same or different and are independently selected from the group listed above;

Y is selected from the group consisting of hydrogen, alkoxy, alkyl, cycloalkyl, cycloalkenyl, heterocyclyl, heterocyclenyl, halogen, heteroalkyl, heteroaryl, —O-cycloalkyl, —$CF_3$, —CN, —C(O)O$R^2$, —C(O)$R^2$, —N($R^2$)$_2$, —OCF$_3$, —OCF$_2$H and —OH, with the proviso that:

when p is 2, 3 or 4, the Y moieties can be the same or different and are independently selected from the group listed above; or when p is 2, the Y moieties can form a cyclic ring of 3 to 7 ring atoms of which 1-2 may be a heteroatom;

Z is selected from the group consisting of hydrogen, alkoxy, alkyl, cycloalkyl, cycloalkenyl, halogen, heteroalkyl, heteroaryl, heterocyclyl, heterocyclenyl, —O-cycloalkyl, —$CF_3$, —CN, —C(O)O$R^2$, —C(O)$R^2$, —N($R^2$)$_2$, —OCF$_3$, —OCF$_2$H; —OH and —S($O_2$)$R^2$, with the proviso that when q is 2, 3, 4 or 5, the Z moieties can be the same or different and are independently selected from the group listed above;

$R^1$ is selected from the group consisting of hydrogen, alkoxy, alkyl, aryl, cycloalkyl, cycloalkenyl, heteroaryl, heterocyclyl, heterocyclenyl, and —N($R^2$)$_2$;

$R^2$ is selected from the group consisting of hydrogen, alkoxy, alkyl, aryl, cycloalkyl, cycloalkenyl, heteroaryl, heterocyclyl, heterocyclenyl, and hydroxyalkyl;

$L^1$ is selected from the group consisting of a covalent bond, —C($F_2$)—, —(CH(O$R^2$))—, —C(O)—, —C(O)N(H)—, —C(=N—O$R^2$)—, —C(=N$R^2$)—, —C(=N—CN)—, —C($R^2$)$_2$—, —N($R^2$)—, —N(H)C(O)—, —N($R^2$)S($O_2$)—, —O—, —OC(O)—, —C(O)O—, —S—, —S($O_2$)—, —S(O)— and —S($O_2$)N($R^2$)—, with the proviso that when $L^1$ is a covalent bond, $M^1$ is directly attached to the phenyl carbon marked A;

$L^2$ is selected from the group consisting of a covalent bond, —C($R^2$)$_2$—, —C(=N—O$R^2$)—, —C(O)—, —C(O)N(H)—, —C(O)O—, —OC(O)—, —N(H)C(O)—, —NHS($O_2$)—, —N($R^2$)—, —O—, —S—, —S(O)—, —S($O_2$)— and —S($O_2$)N($R^2$)—, with the proviso that when $L^2$ is a covalent bond, $M^1$ is directly attached to $M^2$;

$M^1$ is aryl, cycloalkyl, cycloalkenyl, heteroaryl, heterocyclyl or heterocyclenyl; and $M^2$ is alkyl, aryl, cycloalkyl, cycloalkenyl, heteroaryl, heterocyclyl, heterocyclenyl, —C(O)$R^2$, —C(O)O$R^2$, —N($R^2$)$_2$ or —S($O_2$)$R^2$;

with the provisos that:
i) when $M^2$ is —N($R^2$)$_2$, $L^2$ is a covalent bond, —$CH_2$—, —C(O)— or —S($O_2$)— and Z is absent;
ii) when $M^2$ is —C(O)$R^2$ or —C(O)O$R^2$, $L^2$ is a covalent bond, —$CH_2$—, —NH— or —N(alkyl)- and Z is absent (i.e., q is 0);
iii) when $M^2$ is —S($O_2$)$R^2$, $L^2$ is a covalent bond, —$CH_2$—, —NH— or —N(alkyl)- and Z is absent (i.e., q is 0); and
iv) the two $R^2$ moieties of —N($R^2$)$_2$ and —C($R^2$)$_2$— are the same or different and are independently selected, or the two $R^2$ of —N($R^2$)$_2$ are joined together and with the nitrogen to which they are attached to form a heterocyclic ring having 3 to 7 ring atoms optionally containing additionally one or more N or O atoms (such as, for example, morpholine, piperidine and piperazine) wherein said additional N can be optionally substituted with $R^2$;

wherein each of said alkoxy, alkyl, aralkyl, aryl, cycloalkyl, cycloalkenyl, heteroaralkyl, heteroaryl, heterocyclyl, and heterocyclenyl in the definitions above can be unsubstituted or optionally independently substituted with one or more moieties which can be the same or different, each moiety being independently selected from the group consisting of halogen, alkoxy, —$CF_3$, —CN, —$C(O)N(R^2)_2$, —$C(O)OR^2$, —$C(O)R^2$, —$NC(O)R^2$, —$NR^2C(O)OR^2$, —$NR^2C(O)N(R^2)_2$, —$NC(=N-CN)NHR^2$, —$NO_2$, —$N(R^2)_2$, —$OCF_2H$, —$OCF_3$, —OH, —$S(O_2)R^2$ and —$S(O_2)N(R^2)_2$.

The compounds of the present invention can be useful as cannabinoid receptor ligands. The compounds can have anti-inflammatory activity and/or immunomodulatory activity and can be useful in the treatment of various medical conditions including, e.g., cutaneous T-cell lymphoma, rheumatoid arthritis, systemic lupus erythematosus, multiple sclerosis, glaucoma, diabetes, sepsis, shock, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, Crohn's disease, inflammatory bowel disease, reversible airway obstruction, adult respiratory distress syndrome, asthma, chronic obstructive pulmonary disease (COPD) or bronchitis. It is contemplated that a compound of this invention can be useful in treating one or more of the diseases listed.

DETAILED DESCRIPTION

In one embodiment, the present invention discloses cannabinoid receptor ligands represented by structural formula I, or a pharmaceutically acceptable salt or solvate thereof, wherein the various moieties are described above.

In a preferred embodiment of compounds of formula I,
$M^1$ is aryl, heteroaryl or heterocyclyl; and
$M^2$ is aryl, cycloalkyl, heteroaryl, or heterocyclyl.

In another preferred embodiment, X is selected from the group consisting of hydrogen, alkoxy, —$CF_3$, haloalkoxy, halogen, —$OCF_3$, —$OCF_2H$ and —OH.

In another preferred embodiment, Y is selected from the group consisting of hydrogen, alkoxy, alkyl, —$CF_3$, —$C(O)OR^2$, cycloalkyl, halogen, —$N(R^2)_2$, —$OCF_3$, —O-cycloalkyl and —OH.

In another preferred embodiment, Z is selected from the group consisting of hydrogen, alkoxy, alkyl, —$CF_3$, —$C(O)OR^2$, halogen, heterocyclyl, —$N(R^2)_2$, —$OCF_3$, —O-cycloalkyl and —OH.

In another preferred embodiment, $R^1$ is selected from the group consisting of hydrogen, alkoxy, alkyl, cycloalkyl and —$N(R^2)_2$.

In another preferred embodiment, $R^2$ is selected from the group consisting of hydrogen, alkyl, aryl, cycloalkyl and heterocyclyl.

In another preferred embodiment, $L^1$ is selected from the group consisting of —$C(R^2)_2$—, —$N(R^2)S(O_2)$—, —$N(R^2)$—, —$S(O_2)$— and —$S(O_2)N(R^2)$—.

In another preferred embodiment, $L^2$ is selected from the group consisting of a covalent bond, —$C(R^2)_2$—, —$N(R^2)S(O_2)$—, —$N(R^2)$—, —$S(O_2)$— and —$S(O_2)N(R^2)$—.

In another preferred embodiment, $M^1$ is aryl, heteroaryl or heterocyclyl.

In another preferred embodiment, $M^2$ is aryl, cycloalkyl, heteroaryl, or heterocyclyl.

In an additional preferred embodiment, n is 1.

In an additional preferred embodiment, X is hydrogen and/or —OH.

In an additional preferred embodiment, Y is selected from the group consisting of hydrogen, alkoxy, alkyl, —$CF_3$, —$C(O)OR^2$, cycloalkyl, halogen, —$N(R^2)_2$, —$OCF_3$ and —OH.

In an additional preferred embodiment, Z is selected from the group consisting of hydrogen, alkoxy, alkyl, —$CF_3$, —$C(O)OR^2$, halogen, heterocyclyl, —$N(R^2)_2$, —$OCF_3$, —O-cycloalkyl and —OH.

In an additional preferred embodiment, $R^1$ is selected from the group consisting of hydrogen, alkoxy, alkyl, cycloalkyl and —$N(R^2)_2$.

In an additional preferred embodiment, $R^2$ is selected from the group consisting of hydrogen, alkyl, aryl, cycloalkyl and heterocyclyl.

In an additional preferred embodiment, $L^1$ is selected from the group consisting of —C(O)—, —$C(R^2)_2$— and —$S(O_2)$—.

In an additional preferred embodiment, $L^2$ is selected from the group consisting of a covalent bond, —$C(R^2)_2$—, —C(O)— and —$S(O_2)$—.

In an additional preferred embodiment, $M^1$ is aryl, heteroaryl or heterocyclyl.

In an additional preferred embodiment, $M^2$ is aryl, cycloalkyl, heteroaryl, or heterocyclyl.

In a still additional preferred embodiment, n is 1.

In a still additional preferred embodiment, X is hydrogen and/or —OH.

In a still additional preferred embodiment, Y is selected from the group consisting of hydrogen, alkoxy, alkyl, —C(O)$OR^2$, cycloalkyl, —$CF_3$, halogen, —$OCF_3$ and —OH.

In a still additional preferred embodiment, Z is selected from the group consisting of hydrogen, alkoxy, alkyl, —$CF_3$, halogen, —$OCF_3$, —O-cycloalkyl and —OH.

In a still additional preferred embodiment, $R^1$ is selected from the group consisting of hydrogen, alkoxy, alkyl, cycloalkyl and —$N(R^2)_2$.

In a still additional preferred embodiment, $R^2$ is selected from the group consisting of hydrogen, alkyl, aryl and cycloalkyl.

In a still additional preferred embodiment, $L^1$ and $L^2$ are the same or different and are independently —$C(R^2)_2$— or —$S(O_2)$—.

In a still additional preferred embodiment, $M^1$ is aryl or heteroaryl.

In a still additional preferred embodiment, $M^2$ is aryl, cycloalkyl, heteroaryl or heterocyclyl.

A preferred embodiment of compounds has the structure of formula I or a pharmaceutically acceptable salt or solvate thereof, wherein X is selected from the group consisting of hydrogen, alkoxy, —$CF_3$, haloalkoxy, halogen, —$OCF_3$, —$OCF_2H$ and —OH;

Y is selected from the group consisting of hydrogen, alkoxy, alkyl, —$CF_3$, —$C(O)OR^2$, cycloalkyl, halogen, —$N(R^2)_2$, —$OCF_3$, —O-cycloalkyl and —OH;

Z is selected from the group consisting of hydrogen, alkoxy, alkyl, —$CF_3$, —$C(O)OR^2$, halogen, heterocyclyl, —$N(R^2)_2$, —$OCF_3$, —O-cycloalkyl and —OH;

$R^1$ is selected from the group consisting of hydrogen, alkoxy, alkyl, cycloalkyl and —$N(R^2)_2$;

$R^2$ is selected from the group consisting of hydrogen, alkyl, aryl, cycloalkyl and heterocyclyl;

$L^1$ is selected from the group consisting of —C(R²)₂—, —N(R²)—, —S(O₂)— and —S(O₂)N(R²)—;

$L^2$ is selected from the group consisting of a covalent bond, —C(R²)₂—, —N(R²)S(O₂)—, —N(R²)—, —S(O₂)— and —S(O₂)N(R²)—;

$M^1$ is aryl, heteroaryl or heterocycloalkyl;

$M^2$ is aryl, cycloalkyl, heteroaryl, or heterocyclyl; with the proviso that:

the two R² moieties of —N(R²)₂ and —C(R²)₂— are the same or different and are independently selected, or wherein each R² of —N(R²)₂ are joined together and with the nitrogen to which they are attached form a heterocyclic ring having 3 to 7 ring atoms;

wherein each of said alkoxy, alkyl, aralkyl, aryl, cycloalkyl, heteroaralkyl, heteroaryl and heterocyclyl in the definitions above can be unsubstituted or optionally independently substituted with one or more moieties which can be the same or different, each moiety being independently selected from the group consisting of halogen, —CF₃, —CN, —C(O)N(R²)₂, —C(O)OR², —NR²C(O)R², —NR²C(O)OR², —NR²C(O)N(R²)₂, —NC(=N—CN)NHR², —NO₂, —N(R²)₂, —OCF₂H, —OCF₃, —OH, —S(O₂)R² and —S(O₂)N(R²)₂.

Another preferred embodiment of compounds has the structure of formula I or a pharmaceutically acceptable salt or solvate thereof, wherein n is 1;

X is —OH;

Y is selected from the group consisting of hydrogen, alkoxy, alkyl, —CF₃, —C(O)OR², cycloalkyl, halogen, —N(R²)₂, —OCF₃ and —OH;

Z is selected from the group consisting of hydrogen, alkoxy, alkyl, —CF₃, —C(O)OR², halogen, heterocyclyl, —N(R²)₂, —OCF₃, —O-cycloalkyl and —OH;

R¹ is selected from the group consisting of hydrogen, alkoxy, alkyl, cycloalkyl and —N(R²)₂;

R² is selected from the group consisting of hydrogen, alkyl, aryl, cycloalkyl and heterocyclyl;

$L^1$ is selected from the group consisting of —C(O)—, —C(R²)₂— and —S(O₂)—;

$L^2$ is selected from the group consisting of a covalent bond, —C(R²)₂—, —C(O)— and —S(O₂)—;

$M^1$ is aryl, heteroaryl or heterocyclyl; and $M^2$ is aryl, cycloalkyl, heteroaryl, or heterocyclyl.

Another preferred embodiment of compounds has the structure of formula I or a pharmaceutically acceptable salt or solvate thereof, wherein n is 1;

X is —OH;

Y is selected from the group consisting of hydrogen, alkoxy, alkyl, —C(O)OR², cycloalkyl, —CF₃, halogen, —OCF₃ and —OH;

Z is selected from the group consisting of hydrogen, alkoxy, alkyl, —CF₃, halogen, —OCF₃, —O-cycloalkyl and —OH;

R¹ is selected from the group consisting of hydrogen, alkoxy, alkyl, cycloalkyl and —N(R²)₂;

R² is selected from the group consisting of hydrogen, alkyl, aryl and cycloalkyl;

$L^1$ and $L^2$ are the same or different and are independently —C(R²)₂— or —S(O₂)—;

$M^1$ is aryl or heteroaryl; and $M^2$ is aryl, cycloalkyl, heteroaryl or heterocyclyl.

Another preferred embodiment of compounds has the structure of formula II:

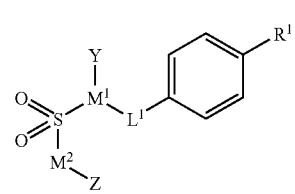

or a pharmaceutically acceptable salt thereof, wherein

Y is selected from the group consisting of hydrogen, alkoxy, alkyl, —CF₃, —CN, —C(O)OR², cycloalkyl, halogen, —N(R²)₂, —OCF₃ and —OH;

Z is selected from the group consisting of hydrogen, alkoxy, alkyl, —CF₃, —C(O)OR², halogen, heterocyclyl, —N(R²)₂, —OCF₃, —O-cycloalkyl and —OH;

R¹ is selected from the group consisting of hydrogen, alkoxy, alkyl, cycloalkyl and —N(R²)₂;

R² is selected from the group consisting of hydrogen, alkyl, aryl and cycloalkyl;

$L^1$ is —C(R²)₂— or —S(O₂)—;

$M^1$ is aryl, indolyl or furanyl; and $M^2$ is aryl, cycloalkyl, heteroaryl or heterocyclyl.

Additionally preferred compounds of formula II above, or a pharmaceutically acceptable salt thereof, are shown below, wherein R¹, L¹, M¹, M², Y and Z are as set forth in the following Table 1:

TABLE 1

| Compd. | R¹ | L¹ | M¹—Y | M²—Z | Y | Z |
|---|---|---|---|---|---|---|
| A | —CH(CH₃)₂ | —CH₂— | 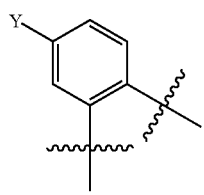 | 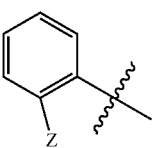 | —CF₃ | F |

TABLE 1-continued
| Compd. | R¹ | L¹ | M¹—Y | M²—Z | Y | Z |
|---|---|---|---|---|---|---|
| B | —CH(CH₃)₂ | —CH₂— | 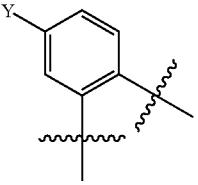 | 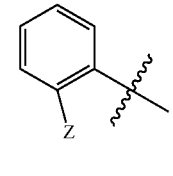 | —CF₃ | 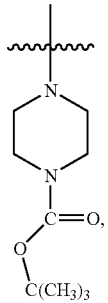 |
| C | —CH(CH₃)₂ | —CH₂— | 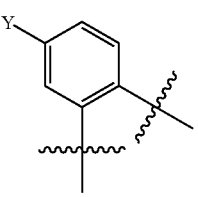 | 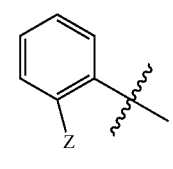 | —OCF₃ | F |
| D | —CH(CH₃)₂ | —CH₂— | 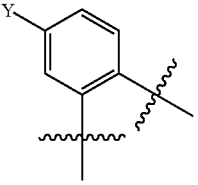 | 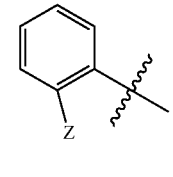 | —OCF₃ | —NH(CH₂)₂OH |
| E | —CH(CH₃)₂ | —S(C₂)— | 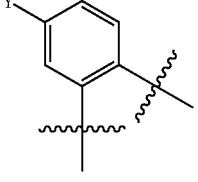 | 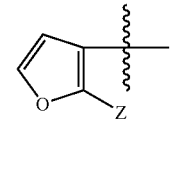 | —OCF₃ | —CH₃ |
| F | —CH(CH₃)₂ | —S(C₂)— | 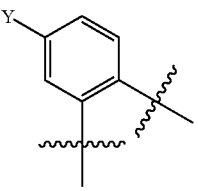 | 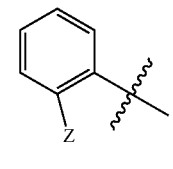 | —OCF₃ | F |
| G | —CH(CH₃)₂ | —S(C₂)— | 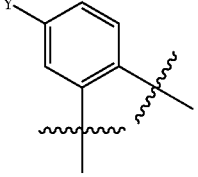 | 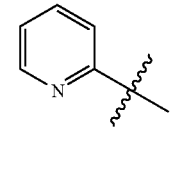 | —OCF₃ | H |
| H | —CH(CH₃)₂ | —S(C₂)— | 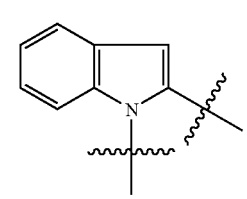 | 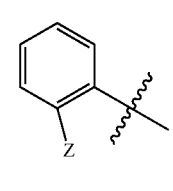 | H | F |

TABLE 1-continued

| Compd. | R¹ | L¹ | M¹—Y | M²—Z | Y | Z |
|---|---|---|---|---|---|---|
| I | —CH(CH₃)₂ | —S(C₂)— | Y-phenyl (1,3-disub) | 2-pyrimidinyl | —OCF₃ | H |
| J | —CH(CH₃)₂ | —CH₂— | N-substituted indol-2-yl | 2-Z-phenyl | H | F |
| K | cyclopropyl | —S(O₂)— | Y-phenyl (1,3-disub) | 2-Z-phenyl | Cl | F |
| L | —CH(CH₃)₂ | —S(O₂)— | N-substituted indol-2-yl | 2-pyridinyl | H | H |
| M | —CH(CH₃)₂ | —S(O₂)— | Y-phenyl (1,3-disub) | 2-Z-phenyl | —N(CH₃)₂ | F |
| N | —CH(CH₃)₂ | —S(O₂)— | 2,3-dihydrobenzofuran-4,5-diyl | 2-pyridinyl | H | H |
| O | —N(CH₃)₂ | —S(O₂)— | Y-phenyl (1,3-disub) | 2-pyridinyl | —CH(CH₃)2 | H |
| P | —CH(CH₃)₂ | —S(O₂)— | Y-phenyl (1,3-disub) | 2-pyridinyl | —N(CH₃)₂ | H |

TABLE 1-continued

| Compd. | R¹ | L¹ | M¹—Y | M²—Z | Y | Z |
|---|---|---|---|---|---|---|
| Q | —CH(CH₃)₂ | —S(O₂)— | Y-phenyl | pyridine N-oxide | —CH(CH₃)₂ | H |
| R | —CH(CH₃)₂ | —S(O₂)— | Y-phenyl | Z-phenyl | —OH | F |
| S | —CH(CH₃)₂ | —S(O₂)— | Y-phenyl | Z-phenyl | —OCH₂CH₂OCH₃ | F |
| T | —CH(CH₃)₂ | Covalent bond | Y-phenyl | piperidine-N-Z | —CH(CH₃)₂ | —CH₃ |
| U | —CH(CH₃)₂ | —S(O₂)— | Y-phenyl | pyridine | morpholine-N- | H |
| V | morpholine-N- | —S(O₂)— | Y-phenyl | pyridine | —CH(CH₃)₂ | H |
| W | cyclopropyl | —S(O₂)— | Y-phenyl | pyridine | —OCH₃ | H |

TABLE 1-continued
| Compd. | R¹ | L¹ | M¹—Y | M²—Z | Y | Z |
|---|---|---|---|---|---|---|
| X | —CH(CH₃)₂ | —S(O₂)— | 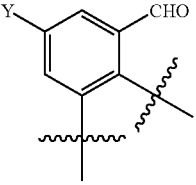 | 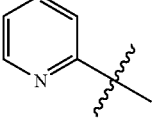 | —CH(CH₃)₂ | H |
| Y | —CH(CH₃)₂ | —S(O₂)— | 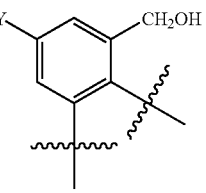 | 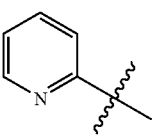 | —CH(CH₃)₂ | H |
| Z | 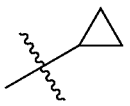 | —S(O₂)— | 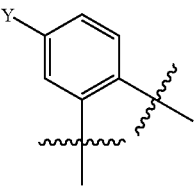 | 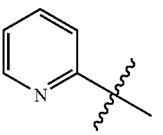 | 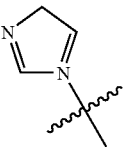 | H |
| AA | 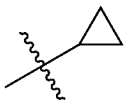 | —S(O₂)— | 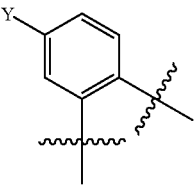 | 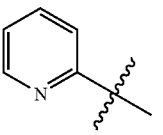 | 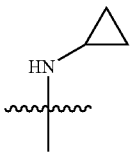 | H |
| AB | —CH(CH₃)₂ | —S(O₂)— | 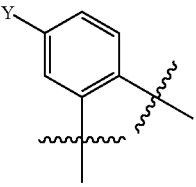 | 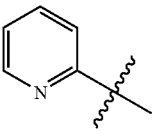 | —CN | H |
| AC | —CH(OH₃)₂ | —S(O₂)— | 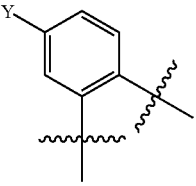 | 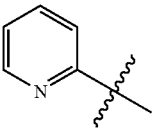 | 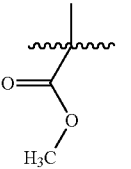 | H |
| AD | —CH(CH₃)₂ | —S(O₂)— | 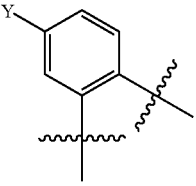 | 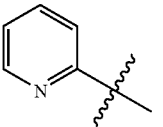 | —CF₃ | H |
| AE | —CH(CH₃)₂ | —S(O₂)— | 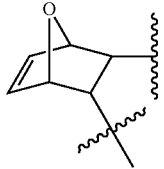 | 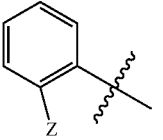 | H | F |

TABLE 1-continued

| Compd. | R¹ | L¹ | M¹—Y | M²—Z | Y | Z |
|---|---|---|---|---|---|---|
| AF | —CH(CH₃)₂ | —S(O₂)— | Y-phenyl (trisubstituted) | phenyl-Z | —OCH₃ | F |
| AG | —CH(CH₃)₂ | —S(O₂)— | Y-phenyl (trisubstituted) | pyridine | —OCH₃ | H |
| AH | cyclopropyl | —S(O₂)— | Y-phenyl (trisubstituted) | phenyl-Z | —OCH₃ | F |
| AI | cyclopropyl | —S(O₂)— | Y-phenyl (trisubstituted) | pyridine | cyclopropyl | H |
| AJ | —CH(CH₃)₂ | —S(O₂)— | Y-phenyl (trisubstituted) | pyridine | —CH(CH₃)₂ | H |
| AK | —CH(CH₃)₂ | —S(O₂)— | Y-phenyl (trisubstituted) | phenyl-Z | —OCH(CH₃)₂ | F |
| AL | —CH(CH₃)₂ | —S(O₂)— | Y-phenyl (trisubstituted) | pyridine | —OCH(CH₃)₂ | H |

TABLE 1-continued
| Compd. | R¹ | L¹ | M¹—Y | M²—Z | Y | Z |
|---|---|---|---|---|---|---|
| AM | —OCH(CH$_3$)$_2$ | —S(O$_2$)— | 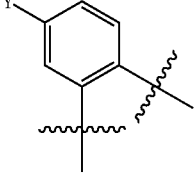 | 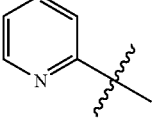 | —CH(CH$_3$)$_2$ | H |
| AN | —CH(CH$_3$)$_2$ | —S(O$_2$)— | 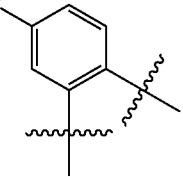 | 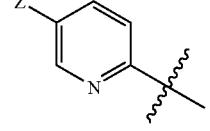 | —OCH(CH$_3$)$_2$ | —COOCH$_3$ |
| AO | —CH(CH$_3$)$_2$ | —S(O$_2$)— | 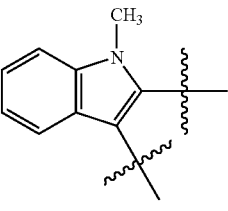 | 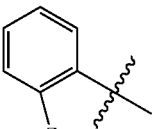 | H | F |
| AP | —CH(CH$_3$)$_2$ | —S(O$_2$)— | 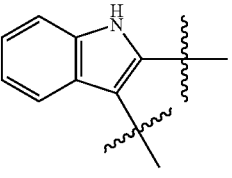 | 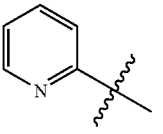 | H | H |
| AQ | —CH(CH$_3$)$_2$ | —S(O$_2$)— | 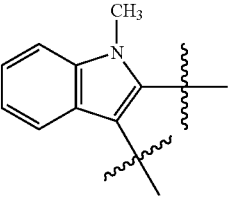 | 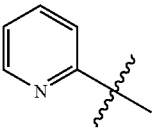 | H | H |
| AR | —CH(CH$_3$)$_2$ | —S(O$_2$)— | 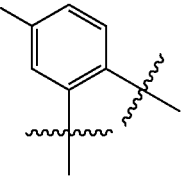 | 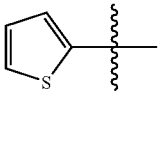 | —CF$_3$ | H |
| AS | —CH(CH$_3$)$_2$ | —S(O$_2$)— | 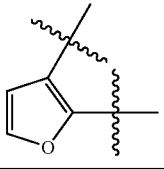 | 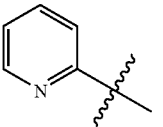 | H | H |
Additional preferred compounds are represented by formula III:

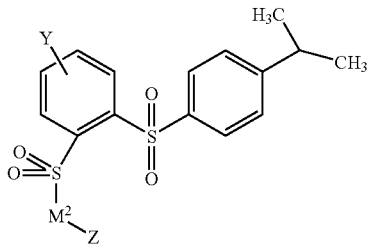

III

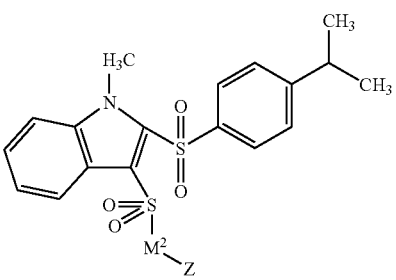

VI or a pharmaceutically acceptable salt thereof, wherein

Y is selected from the group consisting of hydrogen, alkoxy, alkyl, —$CF_3$, cycloalkyl, halogen, —$OCF_3$ and —OH;

Z is selected from the group consisting of hydrogen, alkyl, —$CF_3$, halogen, —$N(R^2)_2$, —$OCF_3$ and —OH; and $M^2$ is aryl or heteroaryl.

Additional preferred compounds are represented by formula IV:

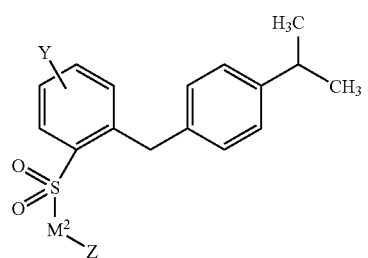

IV or a pharmaceutically acceptable salt thereof, wherein

Y is selected from the group consisting of hydrogen, alkoxy, alkyl, cycloalkyl and —$OCF_3$;

Z is selected from the group consisting of hydrogen, alkyl, —$CF_3$, halogen, —$N(R^2)_2$, —$OCF_3$ and —OH; and $M^2$ is aryl or heteroaryl.

Additional preferred compounds are represented by formula V:

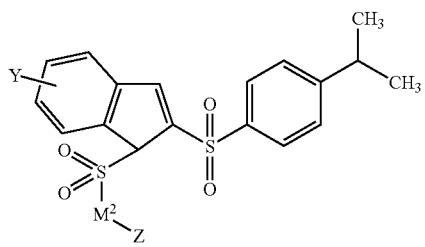

V or a pharmaceutically acceptable salt thereof, wherein

Z is selected from the group consisting of hydrogen, —$CF_3$, halogen, —$OCF_3$ and —OH; and $M^2$ is aryl or heteroaryl.

Additional preferred compounds are represented by formula VI:

or a pharmaceutically acceptable salt thereof, wherein $M^2$ is aryl or heteroaryl; and Z is selected from the group consisting of hydrogen, alkyl, halogen, —$CF_3$, —$N(R^2)_2$, —OH and —$OCF_3$.

Still additional preferred compounds are represented by the following formulae:

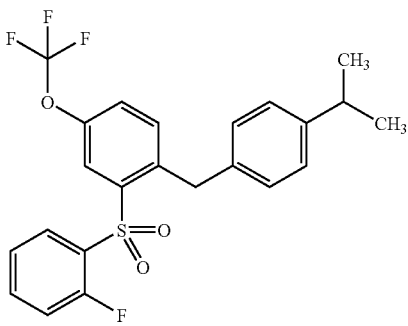

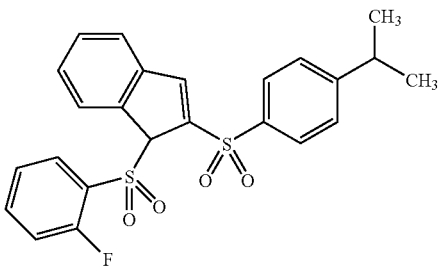

-continued

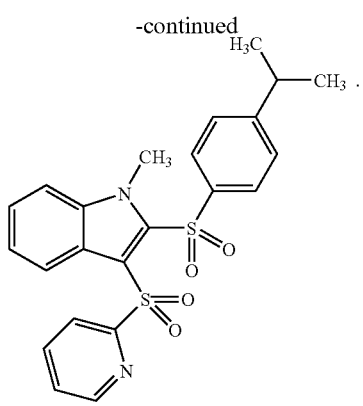

As used above and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy; alkylthio, amino, —NH (alkyl), —NH(cycloalkyl), —N(alkyl)$_2$, carboxy and —C(O) O-alkyl. Non-limiting examples of suitable alkyl groups include methyl, ethyl, n-propyl, isopropyl and t-butyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain, and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Alkylene" means a difunctional group obtained by removal of a hydrogen atom from an alkyl group that is defined above. Non-limiting examples of alkylene include methylene, ethylene and propylene.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyridyl-N-oxide, pyrazinyl, furanyl, thiophenyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b] thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Heteroaryl" also includes tautomers such as, for example,

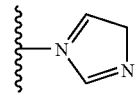

and

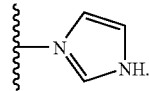

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like. "Cycloalkenyl" means a non-aromatic mono- or multicyclic ring system comprising about 3 to about 10 carbon atoms, preferably about 5 to about 10 carbon atoms, and which contains at least one carbon-carbon double bond. The cycloalkenyl can be optionally substituted with one or more "ring system substituents" which may be the same or different, and are as defined above.

"Halogen" or "halo" means fluorine, chlorine, bromine, or iodine. Preferred are fluorine, chlorine or bromine, and more preferred are fluorine and chlorine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl. "Ring system substituent" also means a cyclic ring of 3 to 7 ring atoms of which 1-2 may be a heteroatom, attached to an aryl, heteroaryl, heterocyclyl or heterocyclenyl ring by simultaneously substituting two ring hydrogen atoms on said aryl, heteroaryl, heterocyclyl or heterocyclenyl ring. Non-limiting examples include:

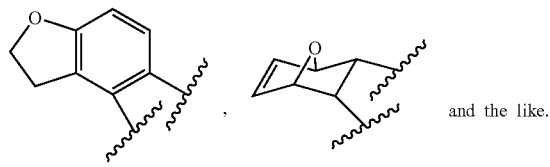

and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" (or "heterocyclic") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, and the like.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

"Halogenated alkyl" or "haloalkyl" means alkyl having 1 or more halogen atoms.

"Heteroalkyl" means straight or branched alkyl chain comprised of from 1 to 12 carbon atoms and 1 or more heteroatoms independently selected from the group consisting of N, O and S.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

It should also be noted that any heteroatom with unsatisfied valences in the text, schemes, examples and Tables herein is assumed to have a hydrogen atom to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York, which is incorporated herein by reference thereto.

When any variable (e.g., aryl, heterocycle, $R^2$, etc.) occurs more than one time in any constituent or in Formulas I, II, III, IV, V or VI, its definition on each occurrence is independent of its definition at every other occurrence.

As a general note to all the Tables that are attached hereto as well as to the Description, Examples and Schemes in this application, any open-ended nitrogen atom with unfulfilled valence in the chemical structures herein refers to NH, or in the case of a terminal nitrogen, —$NH_2$. Similarly, any open-ended oxygen atom with unfulfilled valence in the chemical structures herein refers to —OH and any open-ended carbon atom with unfilled valence is appropriately filled with —H.

As used herein, the term "composition" is intended to encompass a product comprising the specified ingredients in the specified amounts, as well as any product which results, directly or indirectly, from the combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formulas I, II, III, IV, V or VI or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the CDK(s) and thus producing the desired therapeutic, ameliorative, inhibitory or preventative effect.

The compounds of Formulas I, II, III, IV, V or VI can form salts that are also within the scope of this invention. Reference to a compound of Formulas I, II, III, IV, V or VI herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of either Formulas I, II, III, IV, V or VI contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of Formulas I, II, III, IV, V or VI may be formed, for example, by reacting a compound of either Formulas I, II, III, IV, V or VI with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides; lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formulas I, II, III, IV, V or VI, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

The compounds of the present invention can be useful as cannabinoid receptor ligands. The compounds can have anti-inflammatory activity and/or immunomodulatory activity and can be useful in the treatment of various medical conditions including, e.g., cutaneous T-cell lymphoma, rheumatoid arthritis, systemic lupus erythematosus, multiple sclerosis, glaucoma, diabetes, sepsis, shock, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, Crohn's disease, inflammatory bowel disease, reversible airway obstruction, adult respiratory distress syndrome, asthma, chronic obstructive pulmonary disease (COPD) or bronchitis. It is contemplated that a compound of this invention may be useful in treating one or more of the diseases listed.

Additionally, a compound of the present invention may be co-administered or used in combination with disease-modifying antirheumatic drugs (DMARDS) such as methotrexate, azathioprine, leflunomide, pencillinamine, gold salts, mycophenolate mofetil, cyclophosphamide and other similar drugs. They may also be co-administered with or used in combination with NSAIDS such as piroxicam, naproxen, indomethacin, ibuprofen and the like; COX-2 selective inhibitors such as Vioxx® and Celebrex®; immunosuppressives such as steroids, cyclosporin, Tacrolimus, rapamycin and the like; biological response modifiers (BRMs) such as Enbrel®, Remicade®, IL-1 antagonists, anti-CD40, anti-CD28, IL-10, anti-adhesion molecules and the like; and other anti-inflammatory agents such as p38 kinase inhibitors, PDE4 inhibitors, TACE inhibitors, chemokine receptor antagonists, Thalidomide and other small molecule inhibitors of pro-inflammatory cytokine production.

Also additionally, one or more compounds of the present invention may be co-administered or used in combination with at least one H1 antagonist for the treatment of seasonal allergic rhinitis and/or asthma. Suitable H1 antagonists may be, for example, Claritin®, Clarinex®, Allegra®, or Zyrtec®.

In another aspect, the invention provides a method for treating rheumatoid arthritis comprising administering at least one compound of either Formulas I, II, III, IV, V or VI in combination with at least one compound selected from the class consisting of a COX-2 inhibitor e.g. Celebrex® or Vioxx®; a COX-1 inhibitor e.g. Feldene®; an immunosuppressive e.g. methotrexate or cyclosporin; a steroid e.g. β-methasone; and anti-TNF-α compound, e.g. Enbrel® or Remicade®; a PDE IV inhibitor, or other classes of compounds indicated for the treatment of rheumatoid arthritis.

In another aspect, the invention provides a method for treating multiple sclerosis comprising administering at least one compound of either Formulas I, II, III, IV, V or VI in combination with at least one compound selected from the group consisting of Avonex®, Betaseron, Copaxone or other compounds indicated for the treatment of multiple sclerosis.

In another aspect, the invention relates to a pharmaceutical composition comprising a therapeutically effective amount of at least one compound of Formula I, II, III, IV, V or VI in at least one pharmaceutically acceptable carrier.

In yet another aspect, the invention relates to a pharmaceutical composition for treating rheumatoid arthritis comprising a therapeutically effective amount of at least one compound of Formula I, II, III, IV, V or VI in combination with at least one compound selected from the class consisting of a COX-2 inhibitor, a COX-1 inhibitor, an immunosuppressive, a steroid, an anti-TNF-α compound or other classes of compounds indicated for the treatment of rheumatoid arthritis.

In still another aspect, the invention relates to a pharmaceutical composition for treating multiple sclerosis comprising a therapeutically effective amount of at least one compound of Formula I, II, III, IV, V or VI in combination with at least one compound selected from the group consisting of Avonex®, Betaseron, Copazone or other compounds indicated for the treatment of multiple sclerosis.

The compounds of the present invention exhibit anti-inflammatory and/or immunomodulatory activity and can be useful in the treatment of various medical conditions including, e.g., rheumatoid arthritis, systemic lupus erythematosus, multiple sclerosis, glaucoma, diabetes, osteoporosis, renal ischemia, cerebral stroke, cerebral ischemia, nephritis, psoriasis, allergy, inflammatory disorders of the lungs and gastrointestinal tract such as Crohn's disease, and respiratory tract disorders such as reversible airway obstruction, asthma, chronic obstructive pulmonary disease (COPD) and bronchitis. This utility is manifested as demonstrated by activity in the following assay.

Potential cannabinoid receptor ligands were screened for the ability to compete with [$^3$H] CP-55,940 for binding to recombinant cannabinoid receptors. Test compounds were serially diluted in Diluent Buffer (50 mM Tris pH 7.1, 1 mM EDTA, 3 mM $MgCl_2$, 0.1% BSA, 10% DMSO, 0.36% methyl cellulose (Sigma M-6385)) from stocks prepared in 100% DMSO. Aliquots (10 μL) were transferred into 96-well microtiter plates. Membrane preparations of recombinant human cannabinoid $CB_2$ receptor (Receptor Biology #RB-HCB2) or recombinant human cannabinoid $CB_1$ receptor (Receptor Biology #RB-HCB1) were diluted to 0.3 mg/mL in Binding Buffer (50 mM Tris pH 7.2, 1 mM EDTA, 3 mM MgCl$_2$, 0.1% BSA). Aliquots (50 μL) were added to each well of the microtiter plate. The binding reactions were initiated by addition of [$^3$H] CP-55,940 (New England Nuclear # NET 1051; specific activity=180 Ci/mmol) to each well of the microtiter plate. Each 100 μl reaction mixture contained 0.48 nM [$^3$H] CP-55,940, 15 μg membrane protein in binding buffer containing 1% DMSO and 0.036% methyl cellulose. Following incubation for 2 hours at room temperature, the reactions were filtered through 0.5% polyethylenimine-coated GF/C filter plates (UniFilter-96, Packard) with a TomTec Mark 3U Harvester (Hamden, CT). The filter plate was washed 5 times with binding buffer, rotated 180°, then re-washed 5 times with binding buffer. Bound radioactivity was quantitated following addition of 30 μl of Packard Microscint 20 scintillant in a Packard TopCount NXT microplate scintillation counter. Non-linear regression analysis of the resulting data was performed using Prism 2.0b (GraphPad, San Diego, Calif.).

The compounds of the invention exhibit potent affinities for the CB$_2$ receptor as measured by Ki values (in nM). The activities (potencies) for the compounds of the invention are determined by measuring their Ki values. The smaller the Ki value, the more active the compound is for modulating the CB$_2$ receptor. Compounds of the invention exhibit a wide range of activities. The CB$_2$ average Ki values for compounds having one of the Formulae I, II, III, IV, V or VI generally range from >0 nM (e.g., 0.1 nM) to about 1000 nM, preferably about 0.1 nM to about 1000 nM, more preferably about 0.1 nM to about 100 nM, more preferably about 0.1 to about 20 nM, and most preferably less that about 20 nM. Representative compounds of the invention that exhibit excellent CB$_2$ inhibitory activity (Ki values of less than about 20 nanomolar, nM) are as follows: Compounds C, F, G, K, S, AG, AH, AI, AJ, AK, AL, AO, and AQ from Table 1.

The inventive compounds are also highly selective for modulating a CB$_2$ receptor as opposed to modulating a CB$_1$ receptor. A "selective modulator" means that a compound's selection ratio of Ki of the CB, receptor to the Ki of the CB$_2$ receptor is greater than about 100, preferably greater than about 500, more preferably greater than about 1000 and most preferably greater than about 3000.

Compounds of the present invention were found to exhibit CB$_2$ receptor binding activity in the range of 0.1 to 1000 nM.

The present invention also relates to a pharmaceutical composition comprising one or more compounds of Formula I, II, III, IV, V or VI of this invention and one or more pharmaceutically acceptable carriers. The compound of Formulas I, II, III, IV, V or VI, can be administered in any conventional dosage form known to those skilled in the art. Pharmaceutical compositions containing the compound of Formula I, II, III, IV, V or VI can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like. All routes of administration are contemplated including, but not limited to, parenteral, transdermal, subcutaneous, intramuscular, sublingual, inhalation, rectal and topical.

Thus, appropriate unit forms of administration include oral forms such as tablets, capsules, powders, cachets, granules and solutions or suspensions, sublingual and buccal forms of administration, aerosols, implants, subcutaneous, intramuscular, intravenous, intranasal, intraocular, subcutaneous or rectal forms of administration.

When a solid composition is prepared in the form of tablets, e.g., a wetting agent such as sodium lauryl sulfate can be added to micronized or non-micronized compound of Formula I, II, III, IV, V or VI and mixed with a pharmaceutical vehicle such as silica, gelatin starch, lactose, magnesium stearate, talc, gum arabic or the like. The tablets can be coated with sucrose, various polymers, or other appropriate substances. Tablets can be treated so as to have a prolonged or delayed activity and so as to release a predetermined amount of active principle continuously or at predetermined intervals, e.g., by using ionic resins and the like.

A preparation in the form of gelatin capsules may be obtained, e.g., by mixing the active principle with a diluent, such as a glycol or a glycerol ester, and incorporating the resulting mixture into soft or hard gelatin capsules.

A preparation in the form of a syrup or elixir can contain the active principle together, e.g., with a sweetener, methylparaben and propylparaben as antiseptics, flavoring agents and an appropriate color.

Water-dispersible powders or granules can contain the active principle mixed, e.g., with dispersants, wetting agents or suspending agents, such as polyvinylpyrrolidone, as well as with sweeteners and/or other flavoring agents.

Rectal administration may be provided by using suppositories which may be prepared, e.g., with binders melting at the rectal temperature, for example cocoa butter or polyethylene glycols.

Parenteral, intranasal or intraocular administration may be provided by using, e.g., aqueous suspensions, isotonic saline solutions or sterile and injectable solutions containing pharmacologically compatible dispersants and/or solubilizers, for example, propylene glycol or polyethylene glycol.

Thus, to prepare an aqueous solution for intravenous injection, it is possible to use a co-solvent, e.g., an alcohol such as ethanol or a glycol such as polyethylene glycol or propylene glycol, and a hydrophilic surfactant such as Tween® 80. An oily solution injectable intramuscularly can be prepared, e.g., by solubilizing the active principle with a triglyceride or a glycerol ester.

Topical administration can be provided by using, e.g., creams, ointments or gels.

Transdermal administration can be provided by using patches in the form of a multilaminate, or with a reservoir, containing the active principle and an appropriate solvent.

Administration by inhalation can be provided by using, e.g., an aerosol containing sorbitan trioleate or oleic acid, for example, together with trichlorofluoromethane, dichlorofluoromethane, dichlorotetrafluoroethane or any other biologically compatible propellant gas; it is also possible to use a system containing the active principle, by itself or associated with an excipient, in powder form.

The active principle can also be formulated as microcapsules or microspheres, e.g., liposomes, optionally with one or more carriers or additives.

Implants are among the prolonged release forms which can be used in the case of chronic treatments. They can be prepared in the form of an oily suspension or in the form of a suspension of microspheres in an isotonic medium.

The daily dose of a compound of Formula I, II, III, IV, V or VI for treatment of a disease or condition cited above is about 0.001 to about 100 mg/kg of body weight per day, preferably about 0.001 to about 10 mg/kg. For an average body weight of 70 kg, the dosage level is therefore from about 0.1 to about 700 mg of drug per day, given in a single dose or 2-4 divided doses. The exact dose, however, is determined by the attending clinician and is dependent on the potency of the compound administered, the age, weight, condition and response of the patient.

Compounds of the present invention can be used in combination with disease modifying antirheumatic agents described herein above, the administration and dosage of such agents is as according to the schedule listed in the product information sheet of the approved agents, in the Physicians Desk Reference (PDR) as well as therapeutic protocols well known in the art.

Compounds of the present invention can be used in combination with H1 antagonists described herein above, the administration and dosage of such agents is as according to the schedule listed in the product information sheet of the approved agents, in the Physicians Desk Reference (PDR) as well as therapeutic protocols well known in the art.

Compounds of the present invention can be used in combination with compounds useful in the treatment of multiple sclerosis described herein above, the administration and dosage of such agents is as according to the schedule listed in the product information sheet of the approved agents, in the Physicians Desk Reference (PDR) as well as therapeutic protocols well known in the art.

Compounds of the present invention can be used in combination with compounds useful in the treatment of psoriasis described herein above, the administration and dosage of such agents is as according to the schedule listed in the product information sheet of the approved agents, in the Physicians Desk Reference (PDR) as well as therapeutic protocols well known in the art.

It will be apparent to those skilled in the art that the administration of the agents used in combination with the compounds of the present invention can be varied depending on the disease being treated and the known effects of the agents on that disease. Also, in accordance with the knowledge of the skilled clinician, the therapeutic protocols (e.g. dosage amounts and times of administration) can be varied in view of the observed effects of the administered agents on the patients, and in view of the observed responses of the disease to the administered agents.

Compounds of the present invention are generally prepared by processes known in the art, for example, by the processes described below.

The following abbreviations are used in the procedures and schemes: aqueous (aq.), anhydrous (anhyd), n-butyl (n-Bu), n-butyllithium (n-BuLi), tert-butyllithium (t-BuLi), butyllithium (BuLi), sodium t-butoxide (NaOBu$^t$), concentrated (conc.), diethyl ether (Et$_2$O), days (d), 1-(3-dimethylaminopropyl)-3-ethylcarbodiimide hydrochloride (EDCI), dimethylformamide (DMF), ethanol (EtOH), ethyl (Et), ethyl acetate (EtOAc), hours (h), leaving group (LG), hydroxybenzotriazole (HOBT), meta-chloroperoxybenzoic acid (mCPBA), lithium diisopropylamide (LDA), methanesulfonyl chloride (MsCl), methanol (MeOH), palladium bis (dibenzylideneacetone) (Pd(dba)$_2$), minutes (min), methyl (Me), methyllithium (MeLi), molar (moles per liter, M), N-chlorosuccinimide (NCS), N,N-dimethylaminopyridine (DMAP), normal (N), pounds per square inch (psi), preparative thin layer chromatography (PTLC), thin layer chromatography (TLC), room temperature (rt), saturated sodium chloride solution (brine), milliliter (mL), millimole (i.e., 0.001 mole; mmol), milligram (mg), silica gel chromatography (sgc), 2-(tert-butoxycarbonyloxyimino)-2-phenylacetonitrile (BOC-ON), tert-butoxycarbonyl (BOC), trifluoroacetic anhydride (TFAA), trifluoroacetic acid (TFA), trifluoromethanesulfonic anhydride (Tf$_2$O), and tetrahydrofuran (THF). In a typical work-up procedure, the reaction mixture is diluted with a suitable solvent, such as EtOAc, Et$_2$O, or CH$_2$Cl$_2$, and washed successively with appropriate acidic, basic, or neutral aqueous solutions. The organic solution is separated, dried over an appropriate drying agent such as MgSO$_4$ or Na$_2$SO$_4$, filtered, and the solvent removed by evaporation.

General Description of Methods

Compounds of formula I may be preferably prepared as shown in the following reaction schemes. They are preferably prepared as shown in the following reaction schemes. In the reaction schemes, the variables are defined as above.

General Scheme 1
For compounds wherein L$^1$ = -CH$_2$-, -C(O)-, -C =NOR$^2$- and L$^2$ = -S(O$_2$)-, -CH$_2$-, -C(O)-

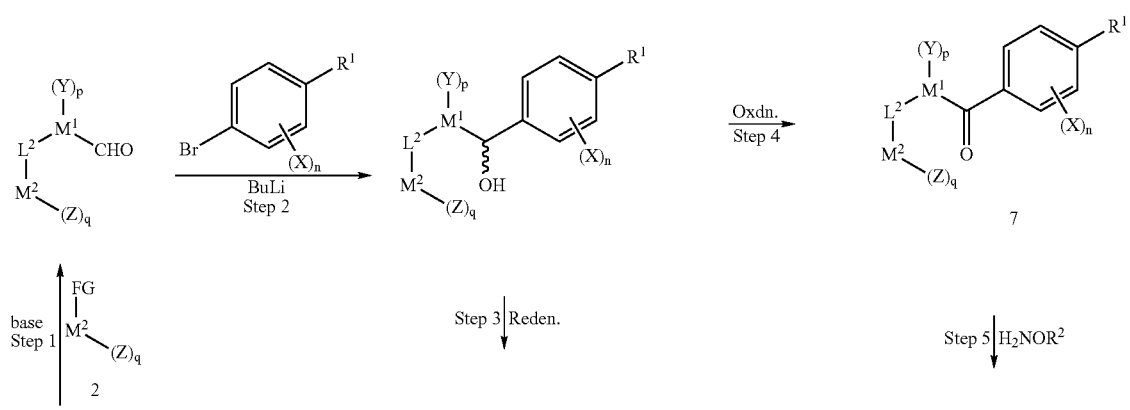

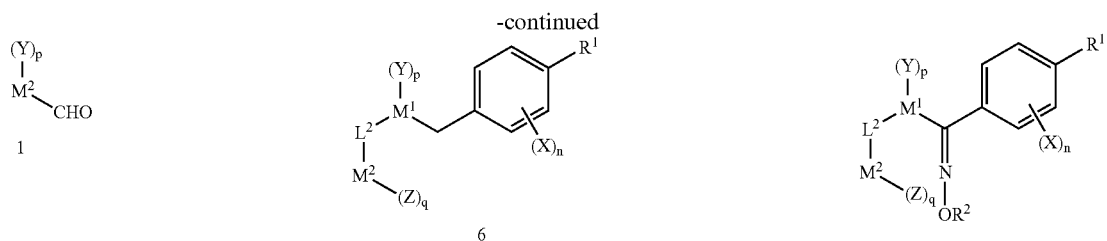

Compounds wherein $L^1$ is one of the following: —$CH_2$—, —C(O)—, —C=$NOR^2$— and $L^2$ is one of the following: —$S(O_2)$—, —$CH_2$—, —C(O)— can be made as shown in Scheme 1.

General Scheme 1

In step 1, an aldehyde of the formula 1 is treated with a base such as LDA, in the presence of N,N,N' trimethylethylenediamine in an inert organic solvent such as THF or DME to generate an ortho anion, and an electrophile of the formula 2 where FG is one of the functional groups e.g., sulfonylfluoride, disulfide, acid chloride, alkylbromide or aldehyde. Preferably, the reaction temperature ranges from –70° C. to 0° C.

The product is purified by silica gel chromatography. In step 2, an aryl bromide of the formula 4 is subjected to halogen metal exchange with a base such as n-BuLi or t-BuLi in an inert solvent such as THF or ether at a low temperature in the range of –78° C. to 40° C. and treated with aldehyde 3 to give an intermediate compound of formula 5. In step 3, intermediate 5 is reduced with triethylsilane in the presence of trifluoroacetic acid to provide a target compound of the formula 6. Additionally, intermediate 5 can be oxidized, e.g., with PCC in methylene chloride, to provide another target compound of the general formula 7. Treatment of 7 with an O-alkylated hydroxylamine in (excess) pyridine provides oxime product 8.

General Scheme 2
For compounds wherein $L^1$ = -S($O_2$)- and $L^2$ = -$CH_2$-, -C(O)-, -S($O_2$)-

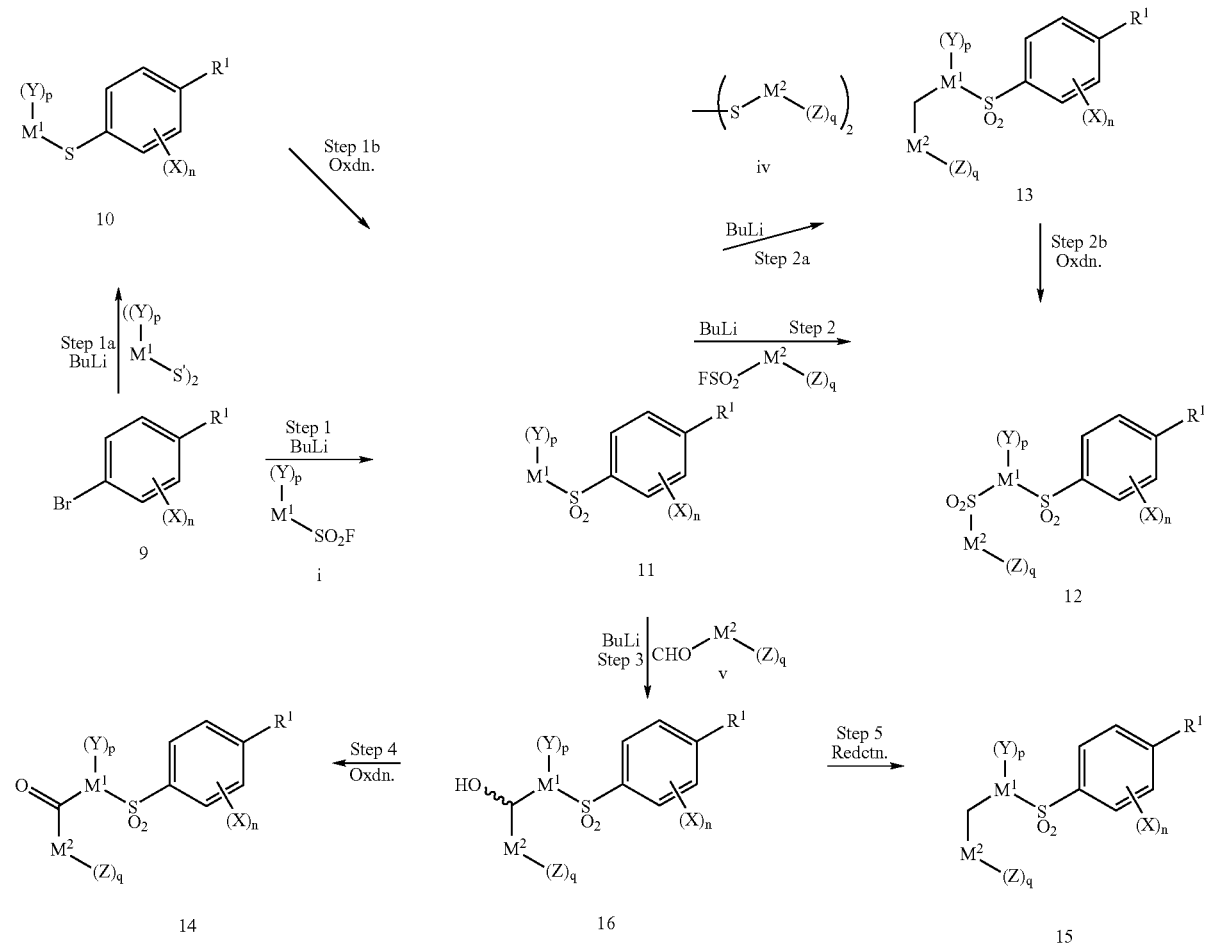

Compounds wherein $L^1$ is —$S(O_2)$— and $L^2$ is one of the following: —$S(O_2)$—, —$CH_2$—, or —$C(O)$— can be prepared as shown in Scheme 2.

General Scheme 2

In step 1, aryl halide 9 is treated with an alkyllithium such as n-butyllithium or t-butyllithium in an inert organic solvent such as THF or DME at −78° C. The resulting aryllithium is then treated with sulfonylfluoride (i) to provide sulfone product 11. Alternatively, the aryllithium is treated with a disulfide (ii) as shown in step 1a to provide sulfide 10, which is then oxidized with a reagent such as mCPBA (step 1 b) to provide product 11. In step 2, product 11 is treated with an alkyl lithium such as n-BuLi or t-BuLi and the resulting ortho anion of 11 is quenched with sulfonyl fluoride (iii) to provide the target molecule 12. Compound 12 can also be prepared by treating the ortho anion of 11 with a disulfide (iv) as shown in step 2a followed by oxidation of the resulting sulfide 13 with mCPBA. Additionally, the ortho anion can be quenched with an aldehyde to obtain alcohol 16 (step 3). In step 4, alcohol 16 can be oxidized to the target 14. The reduced form of alcohol 16, compound 15, can obtained by using a reducing agent such as triethylsilane in the presence of a strong acid such as trifluoroacetic as shown in step 5.

Compounds wherein $L^1$ is —$S(O_2)$— and $L^2$ is —$S(O_2)$— are prepared as shown in Scheme 3.

General Scheme 3

In step 1, starting material 17 is treated with a base such as BuLi, NaH, or $CsCO_3$ followed by compound 18, where LG is a leaving group, preferably a fluoride. The product 19 is treated with an alkyllithium such as nBuLi or t-BuLi at a low temperature, e.g., −100° C. to −78° C., in an inert solvent such as THF or DME, and quenched with sulfonyl fluoride 20 to provide target compound 21. Alternatively, a disulfide 24 is used to quench the anion, thereby providing compound 25. Compound 25 is then oxidized with an oxidizing agent, e.g., mCPBA, to the target 21. Another route to access target 21 involves quenching the anion of 19 with $SO_2$ and treating the resulting lithium salt of sulfonic acid with chlorinating agent such as N-chlorosuccinimde, thereby forming a sulfonyl chloride, which is converted to the corresponding fluoride 22. Compound 22 is then reacted with an aryl lithium reagent formed by reacting 23 with alkyllithium at −78° C. to give target 21.

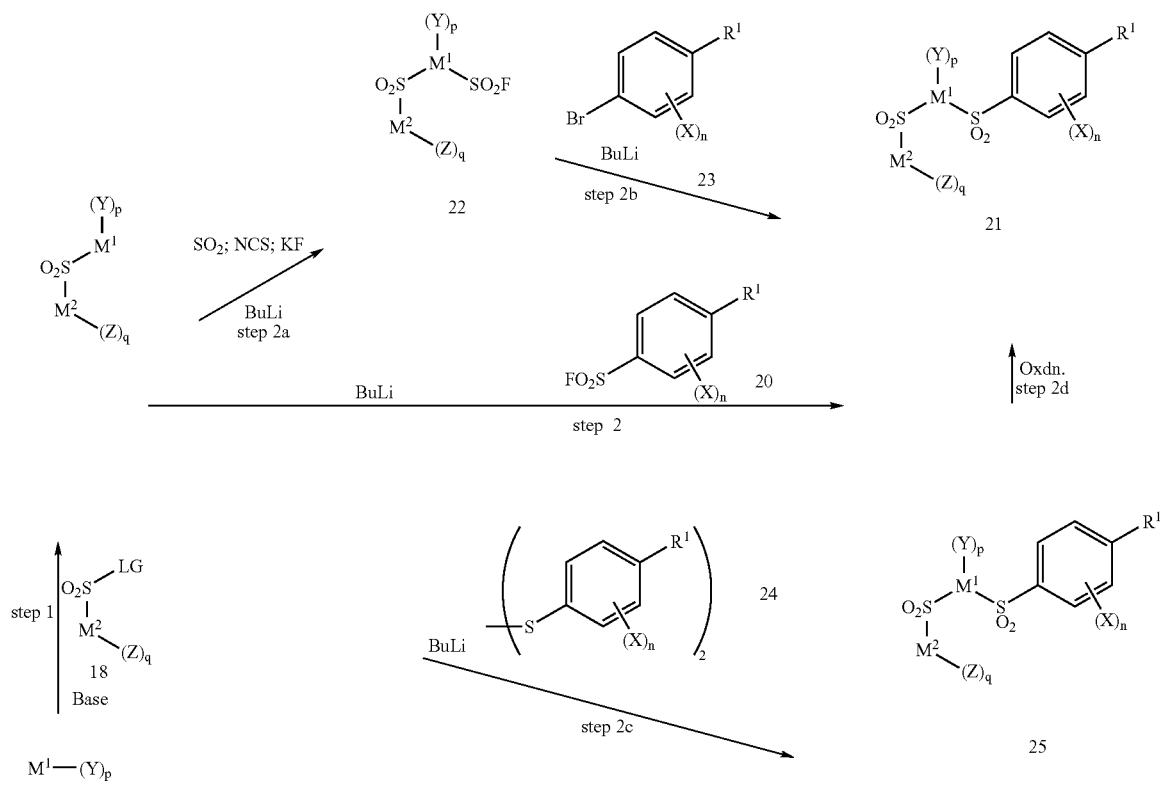

General Scheme 3
For compound wherein $L^1$ and $L^2$ = -$S(O_2)$-

General Scheme 4

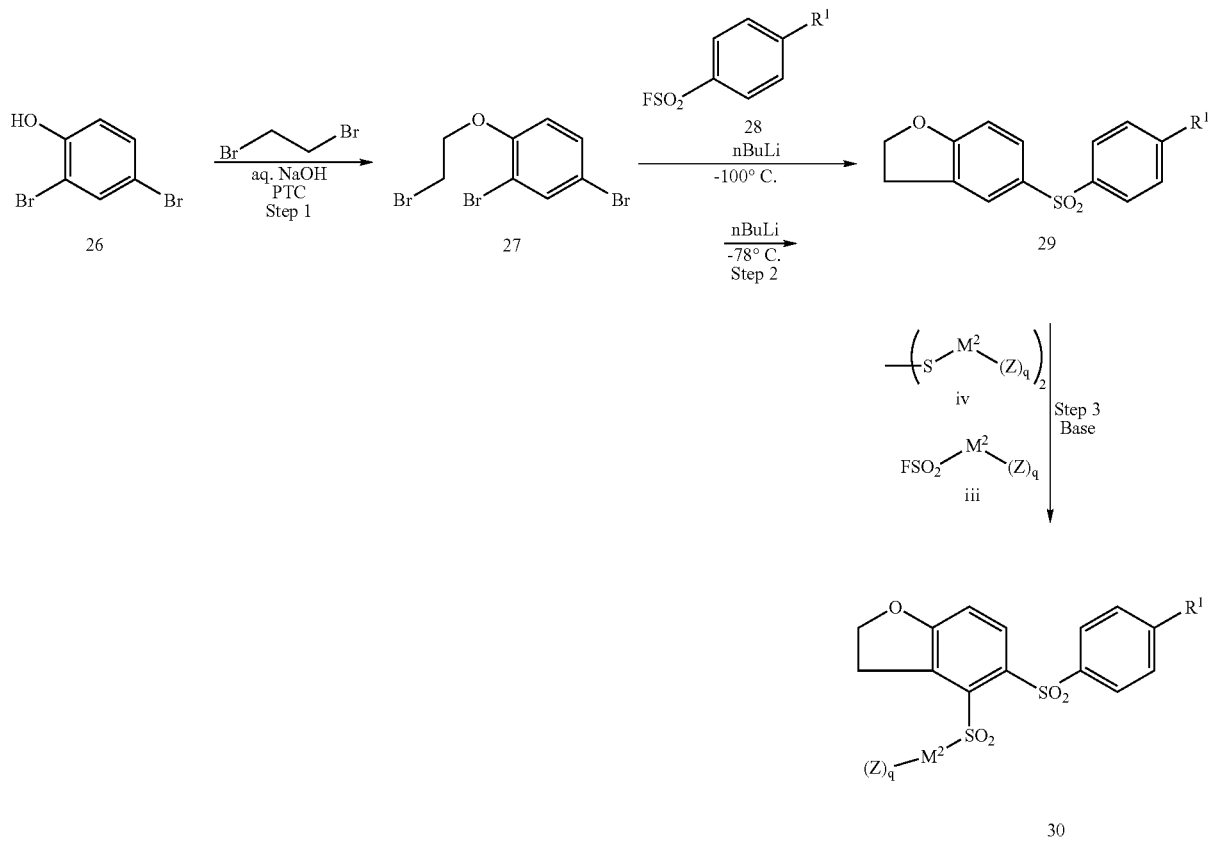

Preparation of Dihydrofuran Compounds: General Scheme 4

In step 1,2,4-dibromophenol 26 and dibromoethane are dissolved in a suitable solvent, such as methylene chloride, dichloroethane, or toluene. Aqueous NaOH is used as a base. The reaction mixture is stirred in the presence of a phase-transfer catalyst (such as tetrabutylammonium hydrogen sulfate, methyl-n-butylammonium chloride, or benzyltriethylammonium hydroxide) between 0° C. and 100° C. for 0.5 to 48 h. The product may be purified via silica gel chromatography or crystallization.

In step 2, the product of step 1 (27) is dissolved in THF or ether and treated with a base such as n-BuLi at −100° C. After stirring, the reaction mixture is treated with another portion of n-BuLi at −78° C. The resulting anion is trapped with the sulphonyl fluoride compound 28 prepared in General Scheme I. The product can be purified via chromatography or crystallization.

In step 3, the product of step 2 (29) is dissolved in THF and treated with a base such as n-BuLi at −78° C. to form a dianion, which is trapped with a suitable electrophile (such as iii/iv). The reaction mixture is quenched with a suitable proton source such as aq NH$_4$Cl or phosphate buffer then extracted with EtOAc. The product 30 may be purified via silica gel chromatography or crystallization.

General Scheme 5

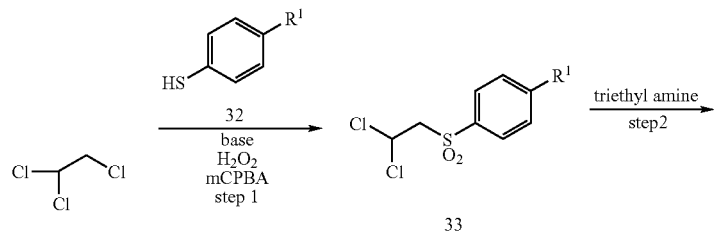

-continued

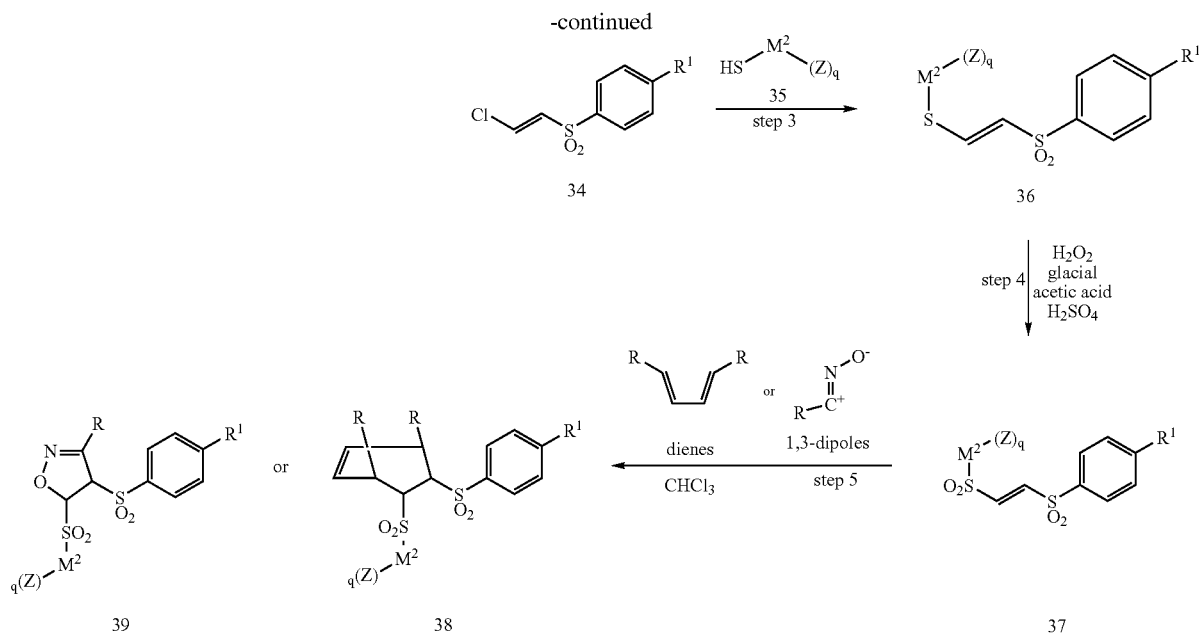

General Scheme 5

In step 1, a mixture of 1,1,2 trichloroethane 31, substituted thiophenol 32, 1 N NaOH and a phase transfer catalyst (such as Aliquat 336, tetrabutylammonium hydrogen sulfate) is stirred for four days. The mixture is then treated with an oxidizing agent (such as $H_2O_2$ or mCPBA) and a catalytic amount of ammonium molybdate. The reaction is then diluted with an organic solvent such as ethyl acetate, methylene chloride, or ether. The organic phase is washed with water and brine and dried. The product 33 is isolated by silica-gel chromatography.

In step 2, product 33 dissolved in methylene chloride at a temperature of 0° C.-15° C. is treated with a base such as triethyl amine, diisopropylamine, or DBU. After stirring for 1 h, the reaction is washed with water, and brine. The product 34 is isolated with silica-gel chromatography.

In step 3, the thiol 35 is dissolved in a solvent such as THF or ether, cooled to 0° C. and treated with a base such as sodium hydride. After stirring for 10-30 min, compound 34 is added as a THF or ether solution and the resulting mixture is allowed to warm to room temperature and the reaction is stirred for 10h. The reaction is quenched with water and worked up. The product is isolated by silica-gel chromatography to provide product 36.

In step 4, product 36 is dissolved in glacial acetic acid and treated with an oxidizing agent such as hydrogen peroxide at 40-60° C. and stirred for 3h. The reaction is cooled and diluted with an organic solvent such as ethylacetate, methylene chloride, or ether and worked up. The product 37 is recrystallized from ether as a white solid.

In step 5 the product 37 is redissolved in $CHCl_3$ and treated with dipoles or dienes to provide cycloaddition products 38 and 39, respectively.

Those skilled in the art will appreciate that similar reactions to those described in the above schemes may be carried out on other compounds of formula I. Starting materials for the above processes are either commercially available, known in the art, or prepared by procedures well known in the art. The following examples illustrate the preparation of some of the compounds of the invention and are not to be construed as limiting the invention disclosed herein. Alternate mechanistic pathways and analogous structures will be apparent to those skilled in the art.

EXPERIMENTAL EXAMPLES

Synthesis of Compound 6B

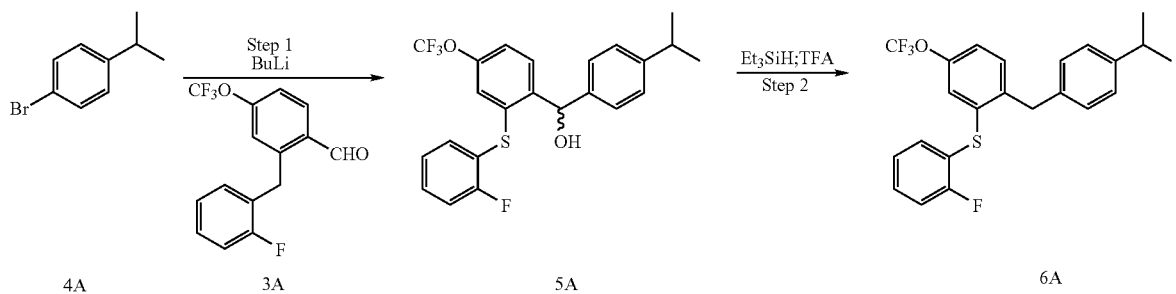

-continued

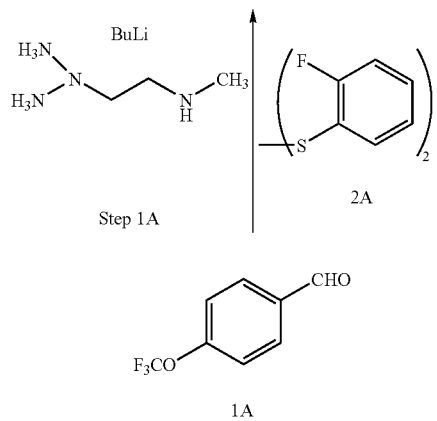

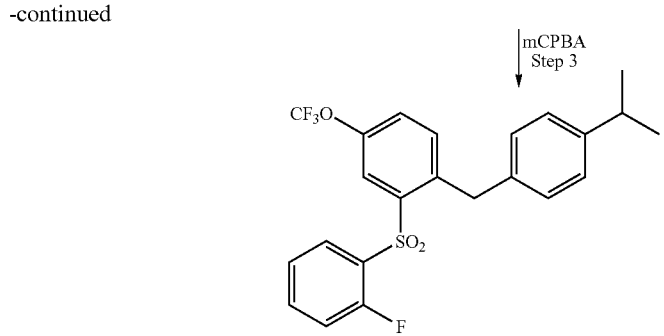

Step 1) n-BuLi (0.66 mL, 2.5 M in hexanes) was added to a solution of 4-bromoisopropylbenzene 4A (0.3 g, 16 mmol) in anhydrous THF (3 mL) at −78° C. The mixture was stirred for 20 minutes and then a THF solution of aldehyde 3A (0.5 g, 1.6 mmol) was added while maintaining the temperature at −78° C. The resulting mixture was stirred for 2h. The reaction was quenched with water, and allowed to warm to 0° C. The product was extracted with 50 mL ethylacetate. The organic phases were washed with 2×25 mL water and 1×25 mL brine and dried over $Na_2SO_4$. The solvent was removed, and the crude product was subjected silica gel preparatory plate chromatography using 20% ethyl acetate/hexane as the eluting solvent to provide 0.5 g of pure product 5A (alcohol).

Step 1A) Aldehyde 3A was prepared using the following procedure: To a solution of N,N,N'-Trimethylethylenediamine (1.2 mL, 8.6 mmols) in THF (8 mL) at −20° C. was added n-BuLi (1.6 M, 5.4 mL, 8.6 mmol) dropwise. After 15 minutes 4-trifluoromethoxybenzaldehyde (1A) (1.5 g, 7.8 mmol) in THF (8 mL) was added. The mixture was stirred for 15 minutes and more n-BuLi (1.6M, 14.6 mL, 23 mmol) was added. The reaction mixture was stirred at −20° C. for 1 h, and then placed in the freezer at −20° C. for 20h. The next day, the mixture was cooled to −40° C., followed by addition of a solution of o-fluorobenzenedisulfide (2A) (4.0 g, 15.7 mmol) in 30 mL THF and stirred at −40° C. to −35° C. for 3 h. The reaction was poured into 0.5 N HCl and extracted with ethyl acetate. The organic layer was washed with water and brine and then dried over $Na_2SO_4$, filtered and concentrated to give a yellow oil. The oil was purified by silica-gel column chromatography (3% ethylacetate/hexanes) to give a light yellow solid 3A, yield 1.55 g (62%).

Step 2) The product 5A from step 1 (0.5 g, 0,001 mol) in 50 mL methylene chloride was treated with triethyl silane (1.83 mL, 0.01 mol) followed by dropwise addition of trifluoroacetic acid (0.097 mL, 0.0011 mol) at ambient temperature. The mixture was stirred for 10 h. The solvent and excess reagents were removed under reduced pressure. The resulting crude product was subjected to preparatory plate silica gel chromatography using ethylacetate:hexane (1:10) as the developing solvent, to provide 0.43 g of pure product 6A.

Step 3) The product 6A from step 2 (0.4 g, 0.00095 mol) in 20 mL methylene chloride was treated with metachloroperoxy benzoic acid (0.87 g, 77%, 0.0035 mol). The mixture was stirred for 20 h, then washed in sequence with 5% aq. sodium bisulfite (20 mL), aq. sodium bicarbonate (2×20 mL), and brine (2×20 mL). The organic phases were dried and concentrated under reduced pressure to yield a crude product which was then purified by preparatory plate silica gel chromatography using ethylacetate:hexane (1:6) as the developing solvent, to provide 0.41 g of pure product 6B.

Synthesis of Compounds 6D and 6E

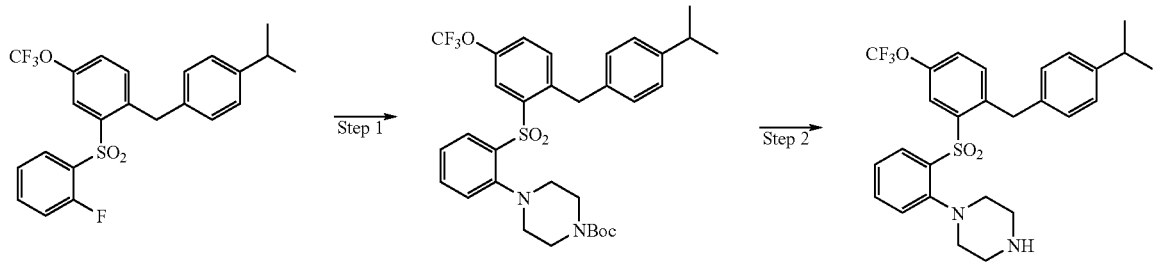

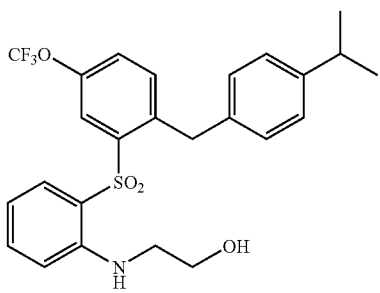

6E

Step 1: Compound 6B (0.3 g; 0.00067) in 20 mL acetonitrile was treated with N-Boc piperazine (0.6 g; 0.0033 mol) and refluxed for 24h. Additional N-Boc piperazine was added (0.6 g; 0.0033 mol) and refluxing was continued for another 24h. The reaction was cooled and the solvent was removed under reduced pressure. The product was isolated by preparatory silica-gel chromatography using ethylacetate:hexane (1:1) to obtain 0.32 g of pure product 6C.

Step 2: Product 6C from Step 1 (0.129 g, 0.0002 mol) in 20 mL methylene chloride was treated with trifluoroacetic acid (0.05 mL, 0.0006 mol) and the mixture was stirred for 3 h at ambient temperature. The reaction was diluted with 20 mL methylene chloride and washed with 5 mL aq. sodium bicarbonate. The organic phases were dried and concentrated to yield pure product 6D (0.08 g).

Synthesis of 6E: Product 6B (0.07 g, 0.000155 mol) dissolved in 10 mL acetonitirile was treated with ethanolamine (0.4 mL) and heated to 80° C. and stirred for 24 h. The solvent was removed under reduced pressure and the crude product was re-dissolved in 30 ml methylene chloride and washed with water (1×20 mL) and brine (1×20 mL). The organics were dried (Na$_2$SO$_4$), filtered, and concentrated. The resulting crude was purified by preparatory plate silica-gel using ethylacetate:hexane (1:2) to give 0.04 g of pure product 6E.

Synthesis of Compounds 12A, 12B and 12C

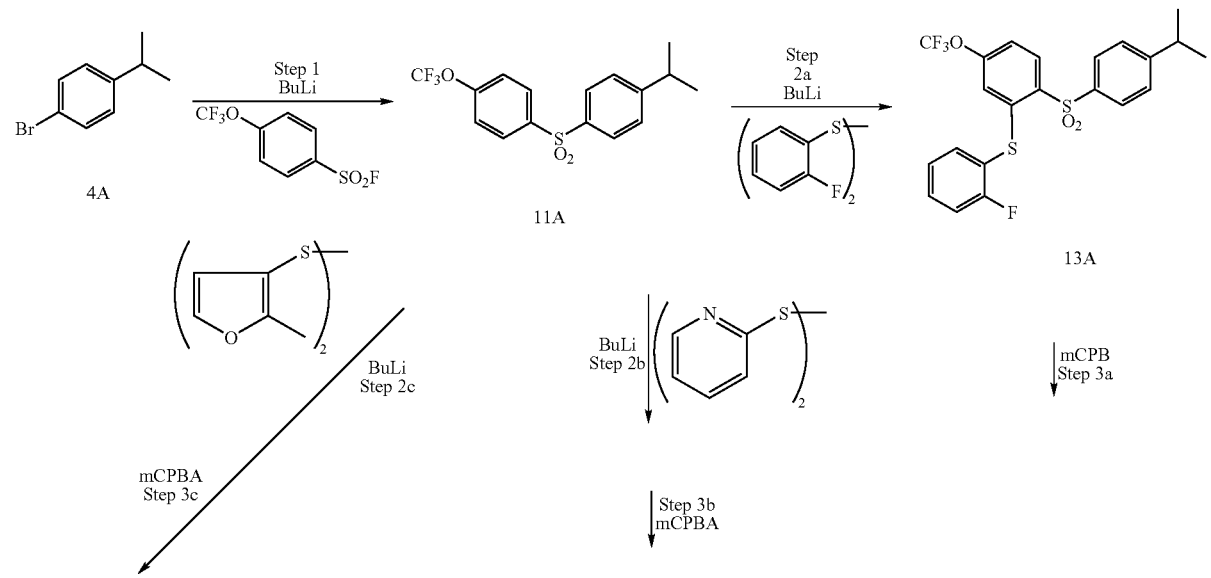

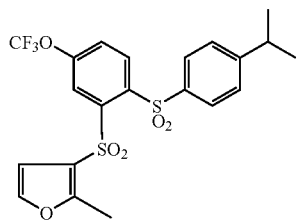

12A

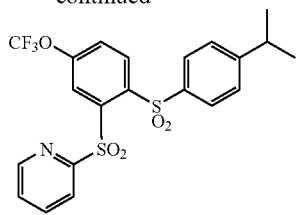

12B

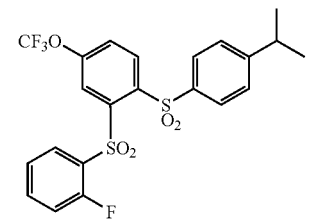

12C

-continued

Step 1: n-Butyl lithium (2.64 mL, 2.24M hexane solution, 0.006 mol) was added dropwise at −70° C. to a dry THF solution (10 mL) of bromo isopropylbenzene 4A (1 g, 0.005 mol). The mixture was stirred for 0.5 h and then a solution of trifluoromethoxybenzene sulfonyl fluoride (1.34 g, 0.0055 mol) as a THF solution (10 mL) was added while maintaining the temperature at −70° C. Stirring was continued for an additional 2 hours. The reaction was quenched with water (5 mL) and extracted with ethylacetate (100 mL). The organic phases were washed with water (2×50 mL) and brine (1×50 mL), dried (Na$_2$SO$_4$), filtered and concentrated to yield a crude product which was isolated by silica gel column chromatography using 10% ethylacetate/hexane as the eluting solvent, resulting in 0.45 g of the product 11A.

Step 2a: The product 11A (0.1 g, 0.00029 mol) of step 1 was dissolved in anhydrous THF (10 mL) and cooled to −70° C. and treated with n-BuLi (0.116 mL, 2.5 M in hexanes, 0.00029 mol). The mixture was stirred for 0.5 h and treated with a THF solution of fluorophenyl disulfide (0.08 g, 0.003 mol 5 mL THF). The resulting mixture was stirred for 2.5 h and the reaction was allowed to warm to −50° C. and then quenched with water (5 ml). The reaction mixture was warmed to room temperature and extracted with 50 mL ethylacetate. The organic phases were washed with water (50 mL), brine (50 mL), and dried over anhydrous Na$_2$SO$_4$. The solvent was removed under pressure and the crude product was subjected to silica-gel preparatory chromatography to provide 0.11 g of pure product 13A.

Step 3a: The product 13A from step 2a (0.066g, 0.00014 mol) was dissolved in methylene chloride (10 mL) and treated with metachloroperoxybenzoic acid (0.12 g, 77%, 0.0007 mol) as a methylene chloride (2 mL) solution. The mixture was stirred for 4 days. The reaction was washed with aq. NaHCO$_3$ (2×20 mL), water (1×20 mL), and brine (1×20 mL). The organic phases were dried over Na$_2$SO$_4$, filtered, and concentrated to yield a crude product. The crude product was purified by silica gel preparatory chromatography using 10% ethylacetate/hexane as the developing solvent to provide 0.039 g of pure product 12C.

Step 2b: The product 11A (0.1 g, 0.00029 mol) of step 1 was dissolved in anhydrous THF (10 mL) and cooled to −70° C. and treated with n-BuLi (0.07 mL, 2.5 M in hexanes, 0.00016 mol). The mixture was stirred for 0.5 h and treated with a THF solution of pyridyl disulfide (0.035 g, 0.00016 mol, 5 mL THF). The resulting mixture was stirred for 2 h and the reaction was allowed to warm to 0° C. and then quenched with water (5 mL). The reaction mixture was warmed to room temperature and extracted with 50 mL ethylacetate. The organic phases were washed with water (50 mL), brine (50 mL), and dried over anhydrous Na$_2$SO$_4$. The solvent was removed under reduced pressure and the crude product was subjected to silica-gel preparatory chromatography using 1:4 ethylacetate:hexane as the developing solvent to provide 0.073 g of pure product.

Step 3b: The product from step 2b (0.035 g, 0.000077 mol) was dissolved in methylene chloride (10 mL) and treated with metachloroperoxybenzoic acid (0.076 g, 77%, 0.0003 mol) as a methylene chloride (2 mL) solution. The mixture was stirred for 2 days. The reaction was washed with aq. NaHCO$_3$ (2×20 mL), water (1×20 mL), and brine (1×20 mL). The organic phases were dried over Na$_2$SO$_4$, filtered, and concentrated to yield a crude product. The crude product was purified by silica gel preparatory chromatography using 10% ethylacetate/hexane as the developing solvent to provide 0.006 g of pure product 12B along with 0.01 g of over-oxidized product, the pyridine N-oxide.

Step 2c: The product 11A of step 1 (0.083 g, 0.00024 mol) was dissolved in anhydrous THF (10 mL) and cooled to −70° C. and treated with n-BuLi (0.106 mL, 2.5 M in hexanes, 0.00026 mol). The mixture was stirred for 0.5 h and treated with a THF solution of methylfuranyldisulfide (0.065 g, 0.0028 mol, 5 mL THF). The resulting mixture was stirred for 2.5 h and the reaction was allowed to warm to −20° C. and then quenched with water (5 mL). The reaction mixture was warmed to room temperature and extracted with 50 mL ethylacetate. The organic phases were washed with water (50 mL), brine (50 mL), and dried over anhydrous Na$_2$SO$_4$. The solvent was removed under pressure and the crude product was subjected to silica-gel preparatory chromatography using 10% ethylacetate/hexane as the solvent to provide 0.09 g of pure product.

Step 3c: The product from step 2c (0.09 g) was dissolved in methylene chloride (10 mL) and treated with metachloroperoxybenzoic acid (0.27 g) as a methylene chloride (2 mL) solution. The mixture was stirred for 4 days. The reaction was washed with aq. NaHCO$_3$ (2×20 mL), water (1×20 mL), and brine (1×20 mL). The organic phases were dried over Na$_2$SO$_4$, filtered, and concentrated to yield a crude product. The crude product was purified by silica gel preparatory chromatography using 25% ethylacetate/hexane as the developing solvent to provide 0.017 g of pure product 12A.

Synthesis of Compound 12F

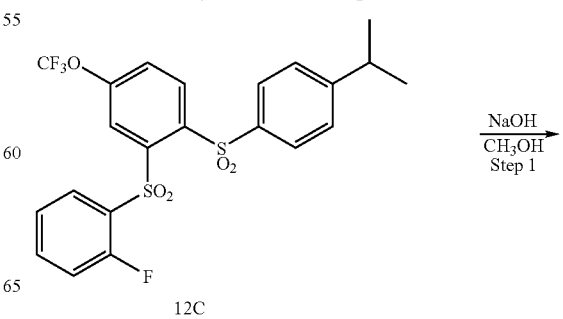

12C

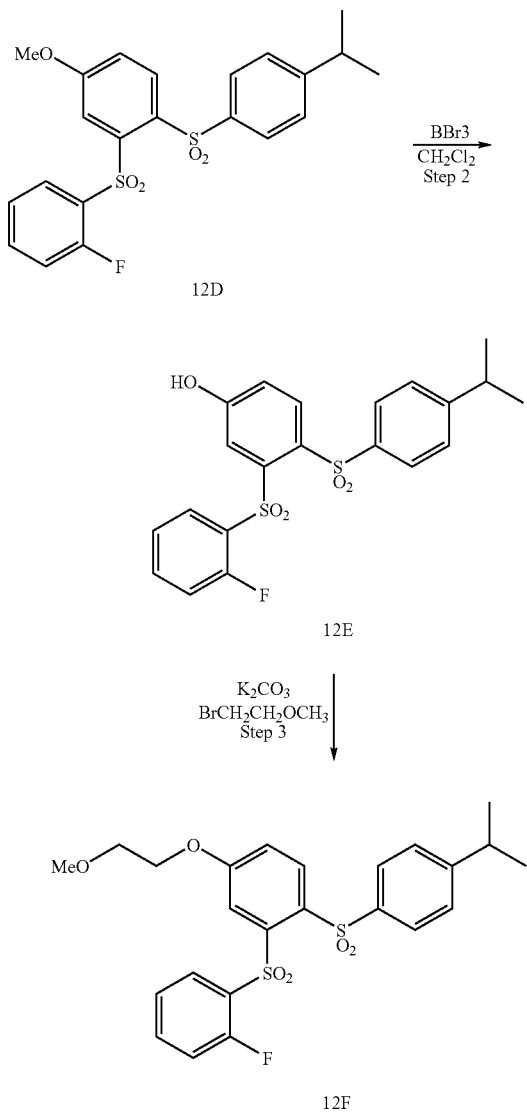

Step 1: Product 12C from step 3a of the above scheme, (0.4 g, 0.00079 mol) was dissolved in 50 mL of $CH_3OH$ and to this solution was added 1 M aq. NaOH (1.8 mL). The resulting mixture was heated at 60° C. for 16h. TLC analysis showed incomplete reaction. Additional 1 M aq. NaOH (0.9 mL) was added and refluxing was continued for 6h. The reaction was cooled and the solvent was removed under reduced pressure. The residue was dissolved in $CH_2Cl_2$ (100 mL) and washed with water (1×50 mL) and brine (1×50 mL). The organic phases were dried ($Na_2SO_4$), filtered, and concentrated to provide a crude product. The product was isolated by silica-gel preparatory plate chromatography using 30% ethylacetate in hexane to yield 0.3 g of pure product 12D.

Step 2: Product 12D from step 1 (0.16 g, 0.00035 mol) dissolved in methylene chloride (10 mL) was cooled to −10° C. and treated dropwise with a 1 M solution of boron tribromide (1.32 mL) The mixture was allowed to warm up to room temperature and stirred for 16h. TLC analysis showed incomplete reaction. Additional boron tribromide (1.32 mL) was added and stirring was continued for 16 h. The reaction was quenched with 5 mL water and diluted with 50 mL methylene chloride. The organic phases were washed with water (1×50 mL), aq. $NaHCO_3$ (1×50 mL), and brine (1×50 mL). The organic phases were dried ($Na_2SO_4$), filtered, and concentrated to yield a crude product. The product 12E was isolated by silica-gel preparatory plate chromatography using 30% ethylacetate/hexanes. Yield: 0.11 g.

Step 3: Product 12E from Step 2 (0.039 g, 0.0000898 mol) in DMF (5 mL) was treated with $K_2CO_3$ (0.015 g, 0.00011 mol) followed by methoxybromoethane (0.0085 mL, 0.000094 mol). The mixture was heated at 50° C. for 24 h. The reaction was diluted with ethylacetate (50 mL) and the organic phases were washed with water (1×50 mL) and saline (1×50 mL). The organic phases were dried ($Na_2SO_4$), filtered, and concentrated to provide a crude product (compound 12F), which was purified by preparatory plate chromatography using 30% ethylacetate/hexanes as the solvent. Yield: 0.009 g.

Synthesis of Compounds 12G and 12H

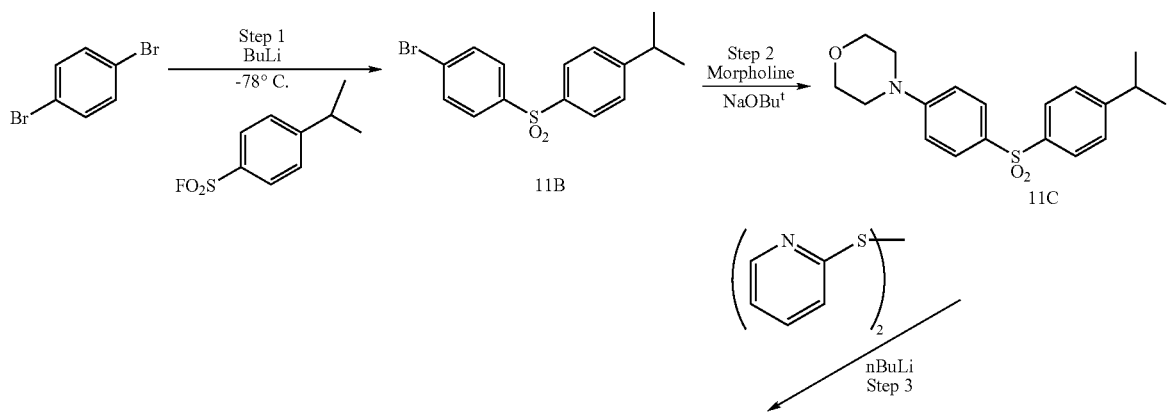

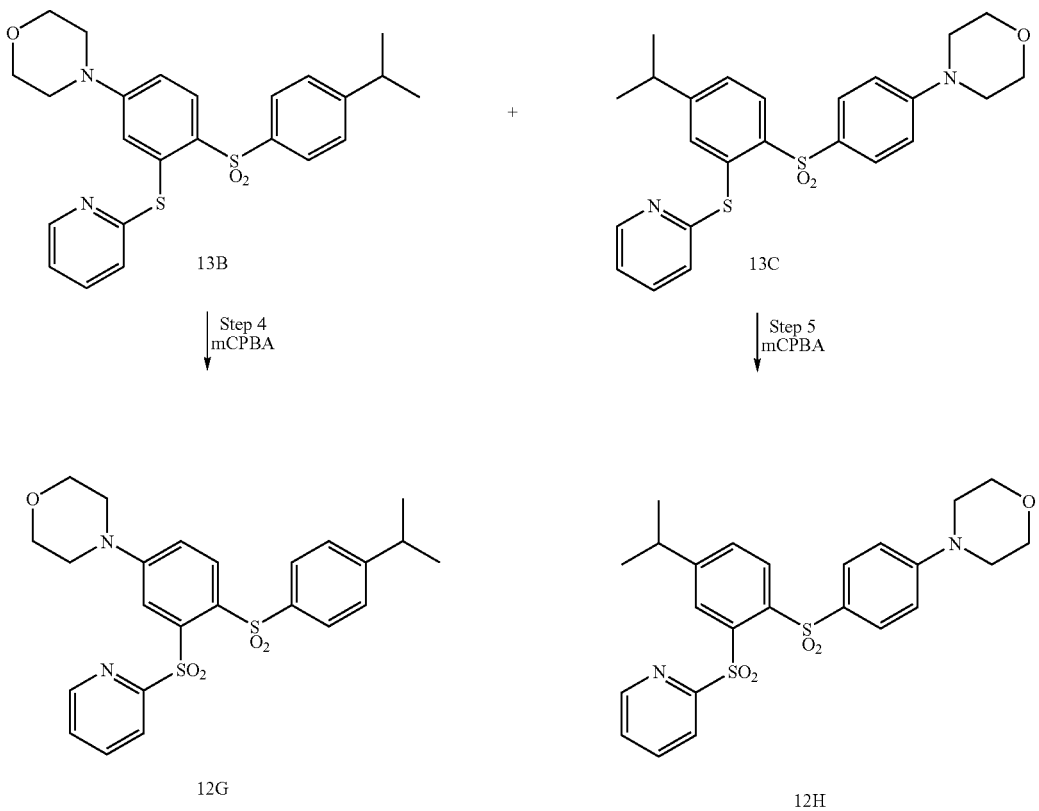

Step 1: Dibromobenzene (5 g, 0.021 mol) was dissolved in 100 mL anhydrous THF and cooled to −70° C. n-BuLi (6.8 mL, 0.0168 mol, 2.5 M) was added and stirred for 1 h, then a THF (10 mL) solution of isopropylbenzene sulfonyl fluoride (4.3 g, 0.021 mol) was added and stirred for 3h, and the temperature was allowed to rise to −30° C. The reaction was quenched with water and the reaction was diluted with ethylacetate (100 mL). The organic phases were washed with water (1×50 mL) and brine (1×50 mL), dried ($Na_2SO_4$) and concentrated to yield a crude product. The product was isolated by silica-gel flash chromatography using 10% ethylacetate/hexane as the eluting solvent to yield 2.1 g of pure product 11B.

Step 2: Product 11B from step 1 was dissolved in 5 mL toluene and NaOBu$^t$ (0.11 g, 0.00114 mol), morpholine (0.092 mL, 0.001 mol), Pd (dba)$_2$ (0.024 g, 0.000026 mol), and P(o-tolyl)$_3$ (0.016 g, 0.00005 mol) were added and the resulting mixture was heated to 100° C. for 24h. The reaction was cooled to room temperature and diluted with ethylacetate (50 mL) and washed with water and brine. The organic phases were dried ($Na_2SO_4$), filtered and concentrated to give a brown oil. The crude product was subjected to silica gel preparatory plate chromatography to yield 0.24 g of pure product 11C.

Step 3: Product 11C from step 2 (0.24 g, 0.00069 mol) was dissolved in 10 mL anhydrous THF and cooled to −70° C. and treated with n BuLi (2.5 M, 0.225 mL, 0.00055 mol). The mixture was stirred for 20 min and then a 5 mL anhydrous THF solution of pyridine disulfide was stirred and the resulting mixture was stirred for 2 h and allowed to warm to 0° C. The reaction was quenched with aq. ammonium chloride and diluted with 50 mL ethyl acetate. The organic phases were washed with water, brine (1×50 mL) dried ($Na_2SO_4$), filtered and concentrated to yield a crude product which was purified by flash chromatography with 5 to 20% ethylacetate/hexanes as the eluting solvent. Two regioisomeric products were obtained. The first fraction yielded 0.09 g of product 13B. The second fraction yielded regioisomeric product 13C 0.1 g.

Step 4: The product 13B (0.066 g, 0.000145 mol) from step 3 was dissolved in 10 mL $CH_2Cl_2$ and treated with mCPBA (70%, 0.095 g, 0.00036 mol). The reaction was stirred for 15 h. The reaction was diluted with 50 mL $CH_2Cl_2$ and washed with aq. $NaHSO_3$ (1×25 mL), aq. $NaHCO_3$ (1×25 mL), and brine (1×25 mL). The organic phases were dried, filtered, and concentrated to yield a crude product that was purified by silica gel preparatory plate using ethyl acetate as the developing solvent to yield: 0.03 g of 12G.

Similarly, Product 13C was oxidized with mCPBA to provide the corresponding sulfone 12H.

Synthesis of Compounds 6F and 7A

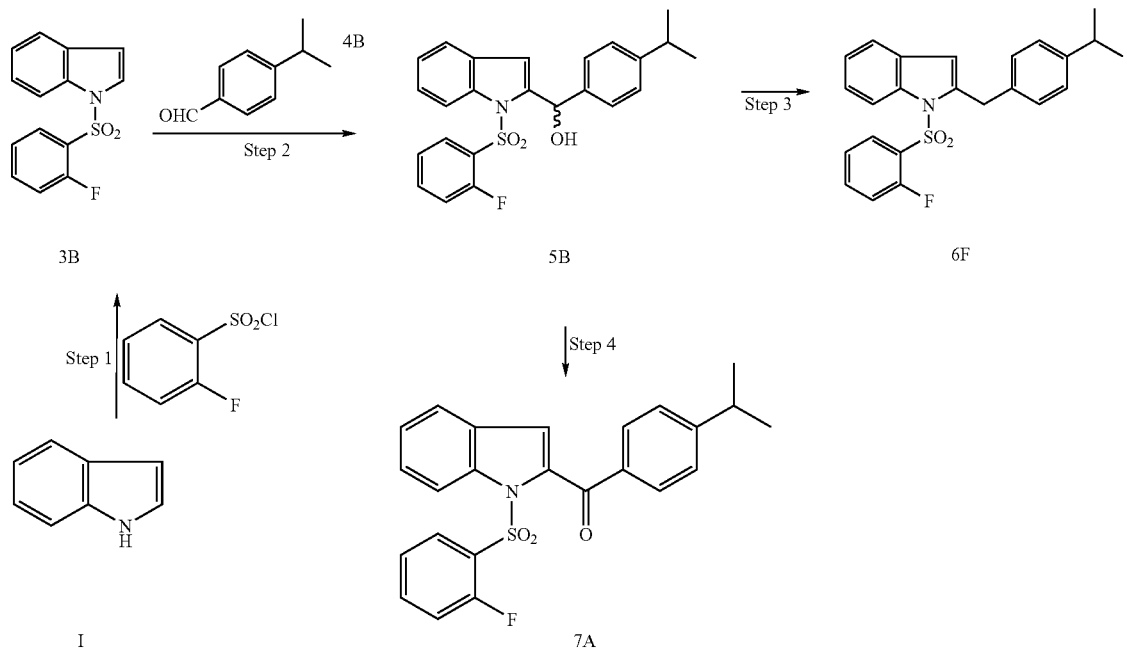

Step 1: NaOH (50 g) was dissolved in H₂O (50 mL). Toluene (100 mL) was added, followed by addition of indole (I) (20 g, 0.17 mol). The resulting mixture was stirred at room temperature for 10 min. 2-Fluorophenylsulphonyl chloride (33 g, 0.17 mol), and tetrabutylammonium hydrogensulfate (cat.) were added. The reaction mixture was stirred at room temperature for 2 h. The aqueous layer was then removed, and the organic layer was washed with brine (3×100 mL). The resulting organic layer was dried over Na₂SO₄ and concentrated to dryness. The crude product was recrystallized using EtOAc (20 mL) and hexanes (70 mL) to give pure compound 3B 40.5 g (86%) as white crystals.

Step 2: Product 3B from step 1(0.462 g, 0.0017 mol) was dissolved in THF (10 mL) and cooled to −78° C. and treated with nBuLi (1.1 eq.). The resulting mixture was stirred for 1.5 h and then isopropylbenzaldehyde 4B (5 mL THF solution) was added and stirred for additional 0.5h. The reaction was quenched with aq. ammonium chloride (10 mL) and allowed to warm to room temperature. The product was isolated with ethyl acetate (100 mL). The organics were dried and concentrated to yield a crude product that was purified by silica-gel chromatography using 9:1 hexane:ethylacetate as the eluting solvent to provide 0.486 g of pure product 5B.

Step 3: The product 5B from Step 2 (0.1 g, 0.0002 mol) in CH₂Cl₂ (20 mL) was treated in sequence with triethylsilane (0.38 mL, 10 eq.) and BF₃.OEt. The mixture was stirred at room temperature for 1 h and then washed with aq. NaHCO₃ (10 mL) and brine (10 mL). The organics were dried and concentrated to yield a crude product that was purified by silica gel preparatory plate chromatography to provide 0.025 g of pure product 6F.

Step 4: The product 5B from Step 2 (0.1 g, 0.0002 mol) in CH₂Cl₂ (30 mL) was treated with celite (1 g) and pyridiniumchlorochromate (PCC) (0.2 g, 0.0008 mol) and the mixture was stirred overnight. The reaction was filtered and the filtrate was washed with aq. NaHCO₃ (1×20 mL) and brine (1×20 mL). The organic phases were dried (Na₂SO₄) and concentrated to yield a crude product that was purified by preparatory plate chromatography using 3:7 ethylacetate:hexane to give 0.026 g of pure product 7A.

Synthesis of Compound 12I

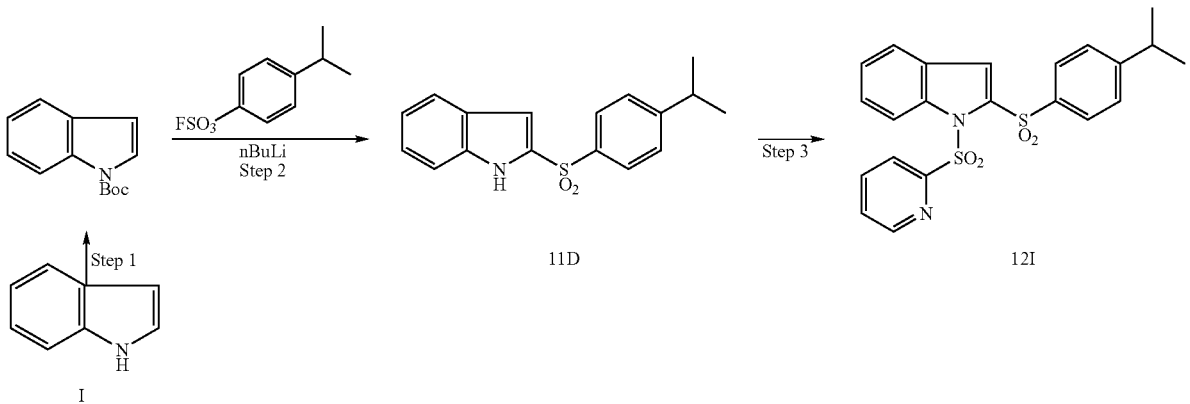

Step 1: Indole (I) (10 g, 0.085 mol) was dissolved in methylene chloride (200 mL). DMAP (cat.) and butoxycarbonyl anhydride (18.7 g, 0.085 mol) was added and the reaction was stirred at room temperature for 10 h. The reaction mixture was washed with aqueous NaCl solution (100 mL). The organic layer was dried over $Na_2SO_4$, and concentrated to dryness. The crude product was purified via silica gel chromatography (25% EtOAc/hexanes) to give 18.6 g (100%) of compound as a light yellow oil.

Step 2: The product from step 1 (1 g, 0.0046 mol) in anhydrous THF (15 mL) at −78° C. was treated with n-BuLi (1.1. eq.) and stirred for 45 min. To this solution was added a THF (5 mL) solution of isopropylbenzenesulfonylfluoride (1 g, 0.05 mol). The resulting mixture was stirred for 4 h and the reaction mixture was allowed to warm to room temperature. The reaction was quenched with aq. NaCl. The organic phases were dried and concentrated to give a crude product, which was purified by silica gel column chromatography using 5:1 hexane:ethylacetate as the eluting solvent. The fractions were collected and concentrated to yield pure product 11D (0.466 g).

Step 3: The product 11D from step 2 (0.143 g, 0.00048 mol) in $CH_2Cl_2$ (5 mL) was treated with NaOH (1 N, 5 mL) and catalytic amounts of tetrabutylammonium hydrogensulfate). To this mixture, pyridylsulfonyl chloride (0.1 g, 0.0006 mol) was added. The reaction was diluted with $CH_2Cl_2$ (50 mL) and washed with water (1×50 mL) and brine (1×50 mL). The organic phases were dried and concentrated to yield a crude product that was purified by chromatography using 4:1 hexane: ethylacetate as the solvent to provide 0.089 g of pure product 12I.

Synthesis of Compounds 12J, 12K and 13D

Step 1: NaH (0.22 g, 95% dry, 8.6 mmol) was dissolved in DMF (20 mL) followed by addition of indole (I) (1 g, 8.5 mmol). The mixture was stirred at room temperature for 10 min. Bis-2-pyridine disulfide (II) (2.17 g, 8.5 mmol) was added as a DMF solution. The reaction mixture was stirred at room temperature for 10 h. The reaction mixture was partitioned between EtOAc and water. The aqueous layer was extracted with additional EtOAc. The combined organic layer was washed with brine, then dried with $Na_2SO_4$ and concentrated to dryness. The crude product was purified by silica gel chromatography (20% EtOAc/hexanes) to give 1.16 g of pure product as a white solid (III).

Step 2: Product from step 1 (0.76 g, 3.3 mmol) and $Boc_2O$ (0.88 g, 4 mmol) were dissolved in methylene chloride (20 mL). DMAP (cat.) was added and the reaction was stirred at room temperature for 4 h. The reaction mixture was washed with aqueous NaCl solution (100 mL). The organic layer was dried over $Na_2SO_4$, and concentrated to give 1.1 g (100%) of the product as a light yellow solid 3C.

Step 3: In a flame-dried flask under $N_2$ blanket, product 3C from step 2 (0.4 g, 1.2 mmol) was dissolved in dry THF (20 mL) and cooled to −78° C. A solution of n-butyl lithium (1.9 M in hexanes, 0.75 mL, 1.4 mmol) was added and the reaction mixture was stirred for 45 min. Isopropylbenzenedisulfide (0.45 g, 1.0 mmol) in THF (1.5 mmol) was added and the reaction mixture was stirred at −78° C. for several hours before it was slowly warmed up to room temperature. The reaction mixture was then quenched with saturated aqueous $NH_4Cl$ (20 mL). Ethyl acetate (30 mL) was added and the layers were separated. The organic layer was washed with brine, then dried over $Na_2SO_4$, and concentrated to dryness.

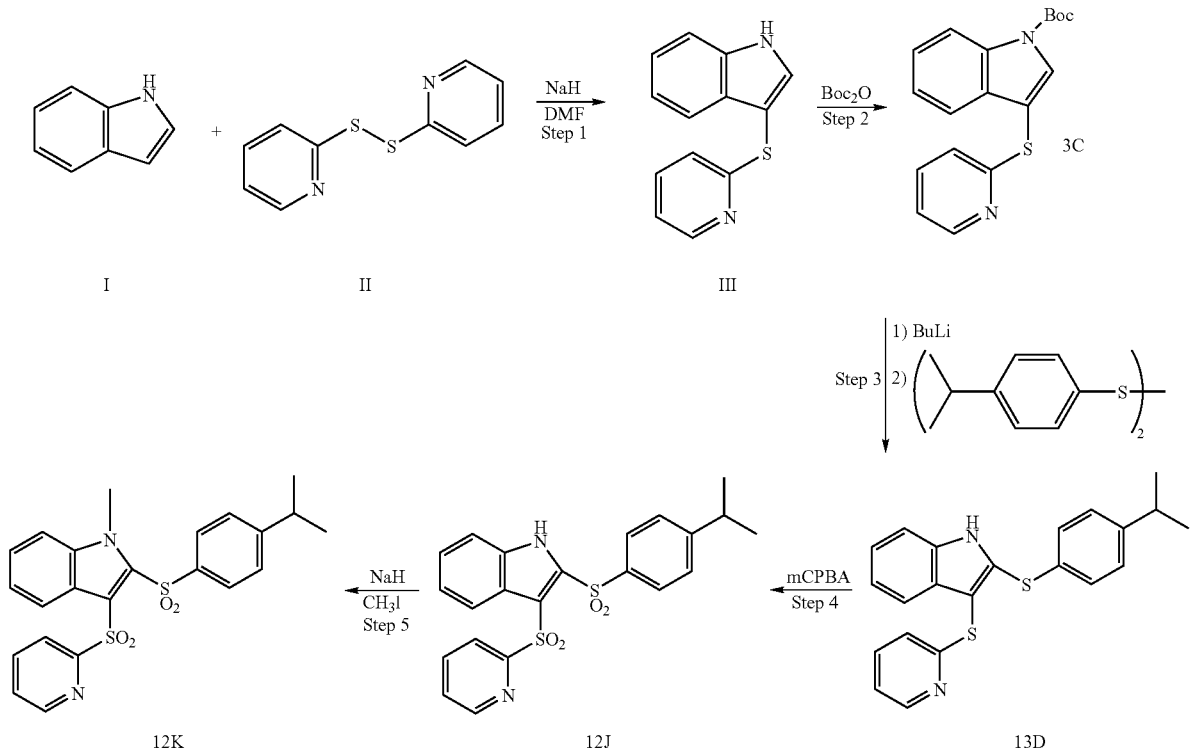

The crude product was purified via silica gel chromatography (11% EtOAc/hexanes) to give 0.135 g (30%) of pure product 13D as a colorless solid.

Step 4: Product 13D from step 3 (115 mg, 0.3 mmol) was dissolved in CH$_2$Cl$_2$ (15 mL) and cooled to 0° C. in an ice bath. mCPBA (410 mg, ca. 1.7 mmol) was added. The ice bath was removed and the reaction mixture was stirred at room temperature overnight. Aqueous NaHCO$_3$ (200 mL) and CH$_2$Cl$_2$ were added and the layers were separated. The organic layer was washed with aq NaHSO$_3$, NaHCO$_3$, H$_2$O, and brine, then dried with Na$_2$SO$_4$. The crude product was purified by silica gel chromatography (33% EtOAc/hexanes) to give 78 mg (58%) of the product 12J as a white solid.

Step 5: NaH (50 mg, 95% dry, 2 mmol) was dissolved in DMF (10 mL) at 0° C. followed by addition of product 12J from step 4 (35 mg, 0.08 mmol). The mixture was stirred at 0° C. for 10 min. CH$_3$I (excess, 1 mL) was added. The reaction mixture was slowly warmed up to room temperature and stirred for 2 h. The reaction mixture was partitioned between EtOAc and water. The aqueous layer was extracted with additional EtOAc (1×50 mL). The combined organic layers were washed with brine, then dried with Na$_2$SO$_4$ and concentrated to dryness. The crude product was purified via silica gel chromatography (33% EtOAc/hexanes) to give 0.34 g (94%) of pure product 12K as a white solid.

Synthesis of Compound 12M quenched with saturated aqueous NH$_4$Cl (20 mL). Ethyl acetate (100 mL) was added and the layers were separated. The organic layer was washed with brine, then dried over Na$_2$SO$_4$, and concentrated to dryness. The crude product was purified via prep. TLC (50% EtOAc/hexanes) to give 0.44 g (42%) of pure product 11 E as a white solid.

Step 2: In a flame-dried flask under N$_2$ blanket, compound 11E (0.44 g, 1.3 mmol) was dissolved in dry THF (20 mL) and cooled to −78° C. A solution of t-butyl lithium (1.5 M in hexanes, 1.7 mL, 2.5 mmol) was added and the reaction mixture was stirred for 15 min. 2-Fluorophenyl disulphide (0.32 g, 1.3 mmol) in THF (5 mL) was added and the reaction mixture was stirred at −78° C. for 1 h before being slowly warmed to 0° C. The reaction mixture was then quenched with saturated aqueous NH$_4$Cl (50 mL). Ethyl acetate (100 mL) was added and the layers were separated. The organic layer was washed with brine, then dried over Na$_2$SO$_4$, and concentrated to dryness. The crude product 13E was used without further purification.

Step 3: Compound 13E (270 mg, 0.57 mmol) was dissolved in CH$_2$Cl$_2$ (15 mL). mCPBA(210 mg, 57-86%, 0.69 mmol) was added and the solution was stirred at room temperature for 1 h. The reaction mixture was diluted with CH$_2$Cl$_2$ (50 mL), washed with NaHSO$_3$ (40 mL) and NaHCO$_3$(50 mL). The organic layers were combined and dried over Na$_2$SO$_4$ and concentrated. The crude material was

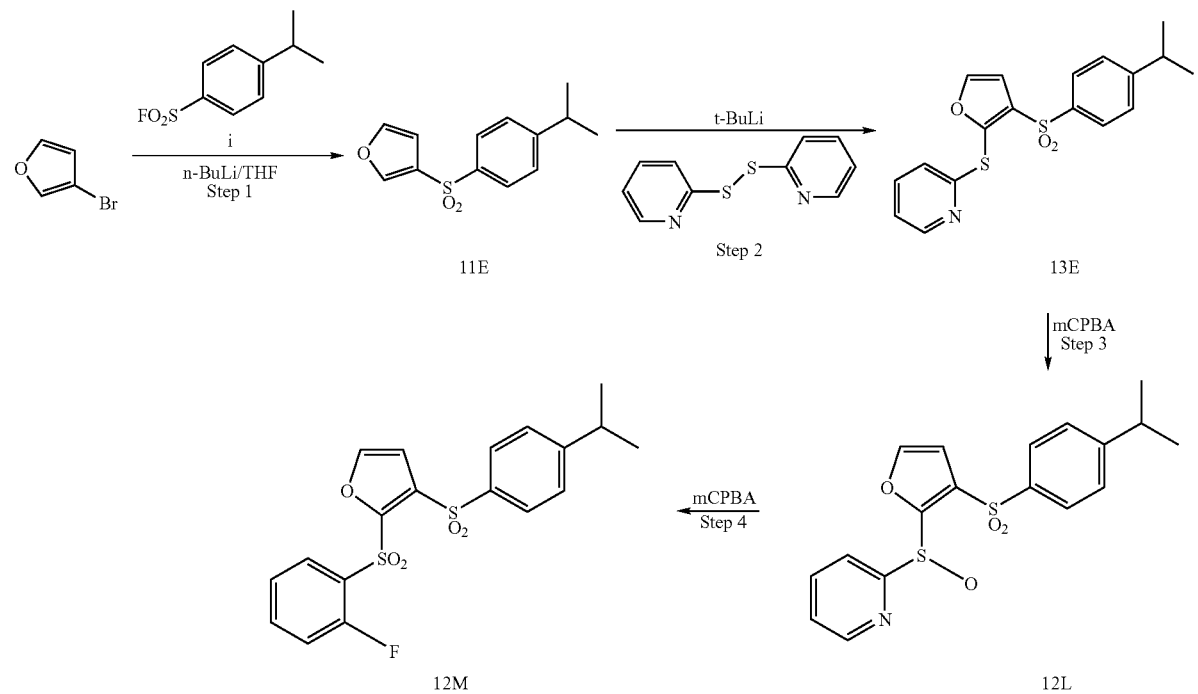

Step 1: In a flame-dried flask under N$_2$ blanket, 3-bromofuran (1.3 g, 9.0 mmol) was dissolved in dry THF (50 mL) and cooled to −78° C. A solution of n-butyl lithium (1.6 M in hexanes, 5.6 mL, 9.0 mmol) was added and the reaction mixture was stirred for 15 min. Isopropylbenzenesulphonyl fluoride (i) (0.90 g, 3.0 mmol) in THF (3 mL) was added to the reaction mixture at −78° C. and stirred for 3 h. The reaction mixture was slowly warmed to room temperature and purified via silica gel chromatography (50% EtOAC/hexanes) to give 120 mg (43%) of compound 12L as a light yellow oil.

Step 4: Compound 12L (70 mg, 0.14 mmol) was dissolved in CH$_2$Cl$_2$ (10 mL). mCPBA (30 mg, 57-86%, 0.10 mmol) was added and the solution was stirred at room temperature, overnight. The reaction mixture was diluted with CH$_2$Cl$_2$ (50 mL), washed with NaHSO$_3$ (40 mL) and NaHCO$_3$(50 mL).

The organic layers were combined and dried over Na$_2$SO$_4$ and concentrated. The crude material was purified via silica gel chromatography (50% EtOAC/hexanes) to give 0.59 g (82%) of 12M as a white solid.

Synthesis of Compound 12N

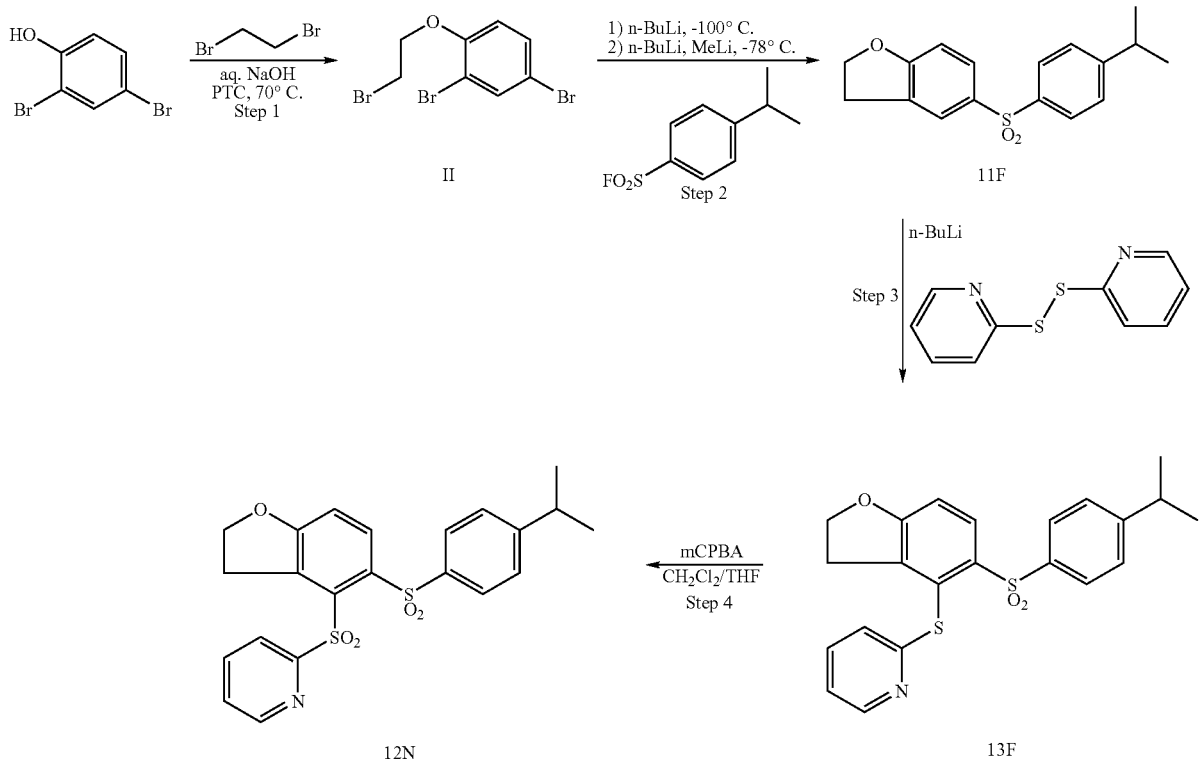

Step 1: A mixture of 2,4-dibromophenyl 1 (5 g, 0.02 mol), 1,2 dibromoethane (37 mL, 0.4 mol), aq. NaOH (14 mL, 3N) Bu$_4$N$^+$HSO$_4^-$ (0.34 g, 1 mmol) was stirred vigorously at 70° C. for 10 h. The mixture was cooled to room temperature. CH$_2$Cl$_2$ (100 mL) was added. The organic layer was washed with NaOH (1 N), HCl (1 N), water and brine, respectively. The organic layer was dried over Na$_2$SO$_4$, and concentrated to dryness. The crude product was purified by recrystallization from ether:hexane to give 3.2 g (45%) of pure compound II as a white solid.

Step 2: In a flame-dried flask under N$_2$ blanket, compound II (1 g, 0.003 mol) was dissolved in dry THF (40 mL) and cooled to −100° C. A solution of n-butyl lithium (2.5 M in hexanes, 1.32 mL) was added and the reaction mixture was stirred for 30 min. The reaction mixture was warmed to −78° C. An additional equivalent of n-BuLi (2.5 M in hexanes, 1.32 mL) was added and the reaction mixture was stirred for 30 min followed by addition of MeLi (1.4 M, 5.6 mL, 7.8 mmol). To the resulting mixture was added isopropylbenzene sulfonyl fluoride (0.72 g, 0.0036 mol) in THF (5 mL) and the reaction mixture was stirred for 2 h before quenching with aq NH$_4$Cl. The reaction was diluted with EtOAc and extracted with water (100 mL) and brine (50 mL), respectively. The organic layer was dried over Na$_2$SO$_4$, and concentrated to dryness. The crude product was purified via preparative thin layer chromatography (40% EtOAc/hexanes) to give 0.98 g (38%) of compound 11F as a white solid.

Step 3: In a flame-dried flask under N$_2$ blanket, compound 11F (0.3 g, 0.001 mol) was dissolved in dry THF (20 mL) and cooled to −78° C. A solution of n-butyl lithium (1.7 M in hexanes, 0.476 mL) was added and the reaction mixture was stirred for 45 min. Pyridine disulphide (0.248 g, 1.25 mmol) in THF (5 mL) was added and the reaction mixture was stirred at −78° C. for 2 h before being slowly warmed to room temperature. The reaction mixture was then quenched with saturated aqueous NH$_4$Cl (50 mL). Ethyl acetate (100 mL) was added and the aqueous and organic layers were separated. The organic layer was washed with brine, then dried over Na$_2$SO$_4$, and concentrated to dryness. The crude product was purified via silica gel chromatography (25% EtOAc/hexanes) to give 0.28 g (48%) of compound 13F as a white powder.

Step 4: Compound 13F (0.28 g, 0.7 mmol) was dissolved in CH$_2$Cl$_2$ (50 mL) with trifluroacetic acid (0.2 mL). mCPBA (0.358 g, 57-86%) was added and the solution was stirred at room temperature, overnight. The reaction mixture was taken up in CH$_2$Cl$_2$, washed with NaHSO$_3$ (40 mL) and NaHCO$_3$ (50 mL). The organic layers were combined and dried over Na$_2$SO$_4$ and concentrated. The crude material was purified via silica gel chromatography (50% EtOAC/hexanes) to give 0.09 g (42%) of compound 12N as a white foam.

Synthesis of 38A

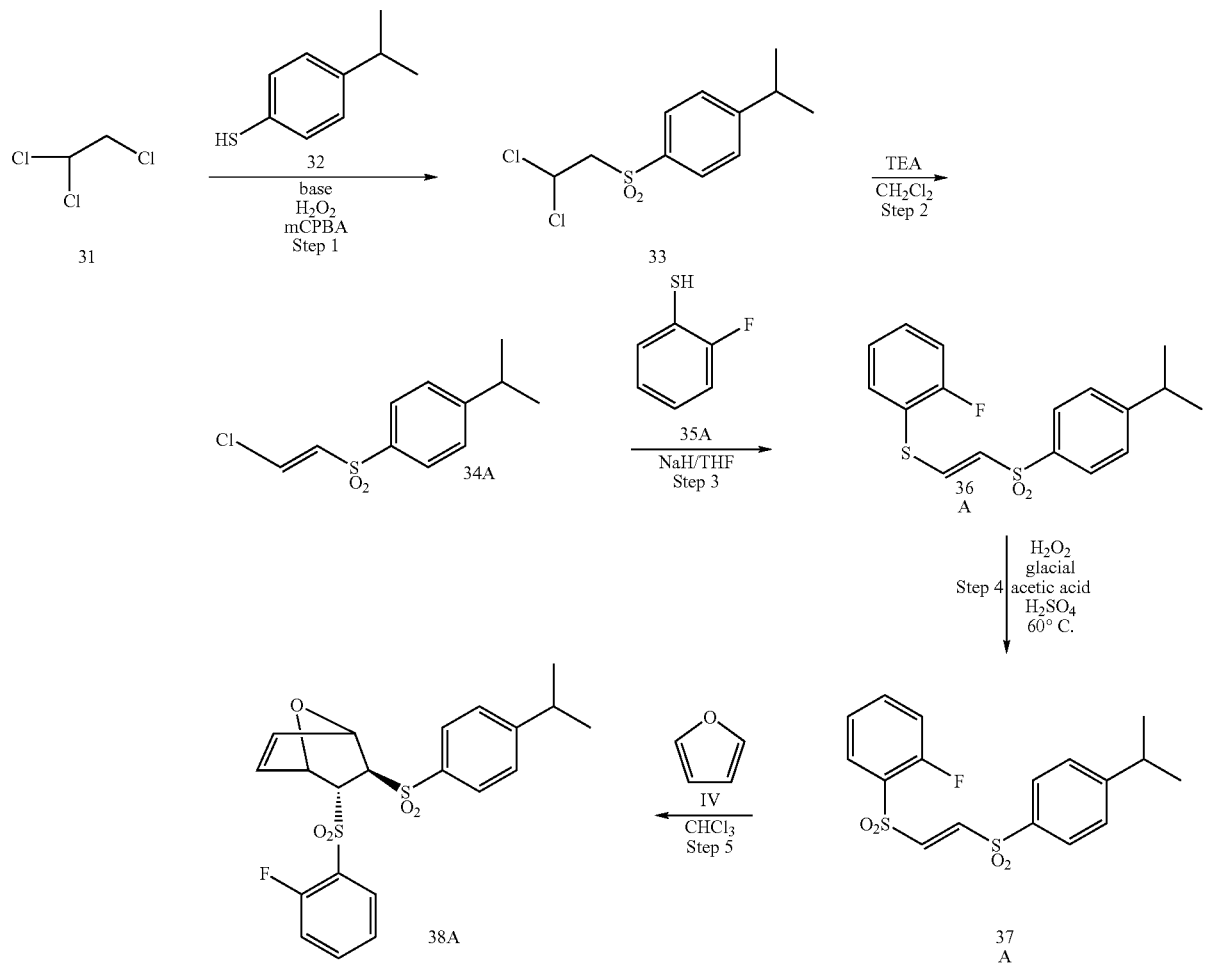

Step 1: A mixture of 1,1,2 trichloroethane 31 (10 mL), isopropyl thiophenol (2.19 g, 0.014 mol), 1N NaOH (16 mL, 0.016 mol), and Aliquat® (tricaprylylmethyl ammonium chloride; 0.01 g; catalytic) were stirred for 4 days. The reaction was diluted with 50 mL of $CH_3OH$ and cooled to 0° C. and then $H_2O_2$ was added dropwise (14 mL, 30%) followed by ammoniummolybdate (0.1 g, catalytic). The mixture was stirred vigorously for 24h. TLC analysis showed the formation of two products. The reaction was diluted with 100 mL ethylacetate and washed with 2×50 mL of water and 1×50 mL of brine. The organic phases were dried and concentrated to provide a crude product which was subjected to flash column chromatography using 10% ethylacetate:hexane as the eluting solvent. Appropriate fractions were collected and concentrated to provide 1.1 g (4 mmol) of half-way oxidized sulfoxide product which was dissolved in 50 mL methylene chloride at 0° C. and treated with metachloroperoxybenzoic acid (0.776 g, 4.5 mmol) and stirred for 2 days. TLC analysis showed complete conversion to the desired sulfone 33A. The solvent was removed under reduced pressure and the product redissolved in ethylacetate (100 mL). The organic phases were washed with aq. $NaHCO_3$ (4×50 mL) and brine (1×50 mL), dried ($MgSO_4$) and concentrated to provide pure product 33A.

Step 2: Product 33A from step 1 (1.1 g, 4 mmol) in 50 mL $CH_2Cl_2$ was cooled to 0° C. and treated with triethylamine (0.6 mL, 4.4 mmol). The mixture was stirred for 1 h. The solvent was removed and the crude product Was redissolved in 100 mL ethylacetate and washed with water (2×50 mL) and brine (1×50 mL), dried, and concentrated to yield pure product 34A.

Step 3: 2-Fluorobenzene thiol (0.57 g, 4.4 mmol) in anhydrous THF (25 mL) at 0° C. was treated with NaH (0.17 g, 60% oil dispersion, 4.4. mmol). The mixture was stirred for 10 min and then chlorovinyl sulfone 34A (0.9 g, 3.7 mmol) was added as a 5 mL THF solution. The mixture was allowed to warm up to room temperature and stirring was continued for 10h. The reaction was cooled to 0° C. and quenched with water (5 mL). The resulting mixture was diluted with ethyl acetate (100 mL) and the organics were washed with water (2×50 mL) and brine (1×50 mL). The organics were dried and concentrated to yield a crude product, which was subjected to silica gel chromatography using 10% ethylacetate/hexane as the eluting solvent. The fractions were collected and concentrated to yield pure product 36A.

Step 4: Product 36A from step 3 (0.28 g, 0.8 mmol) was dissolved in glacial acetic acid (10 mL), cooled to 0° C. and treated with $H_2O_2$ (3 mL, 30% water) and conc. $H_2SO_4$ (2 mL). The mixture was allowed to warm to room temperature and heated to 60° C. for 3h. The reaction was cooled to room temperature and diluted with 50 mL ethylacetate. The organic phase was washed with water (3×50 mL) and brine (1×50 mL). The organic phases were dried and concentrated to yield a solid product, which was recrystallized from ether as white solid 37A.

Step 5: Product 37A from step 4 (0.15 g, 0.4 mmol) and furan (IV) (0.15 g, 2 mmol) in 2 mL chloroform were stirred for 10 h. The solvent was removed and the addition of $CH_3OH$ (5 mL) led to precipitation of product 38A as a white solid. The product was a mixture of inseparable stereoisomers.

TABLE 2

Spectral Data for selected Compounds in Table 1

| Cmpd. | $R^1$ | $L^1$ | $M^1$—Y | $M^2$—Z | Y | Z | MS |
|---|---|---|---|---|---|---|---|
| A | —CH(CH$_3$)$_2$ | —CH$_2$— | | | —CF$_3$ | F | 435.1 (M − 1, 100), 436.1 (M, 50), 459 (M + 23, 12) |
| B | —CH(CH$_3$)$_2$ | —CH$_2$— | | | —CF$_3$ | piperazine-N-C(=O)-O-C(CH$_3$)$_3$ | 603 (M + 1, 100), 547 (63) |
| C | —CH(CH$_3$)$_2$ | —CH$_2$— | | | —OCF$_3$ | F | 453 (M + 1, 13.54), 470.1 (74) 475 (85) |
| D | —CH(CH$_3$)$_2$ | —CH$_2$— | | | —OCF$_3$ | —NH(CH$_2$)$_2$OH | 453 (M + 1, 13.54), 470.1 (74), 475 (85) |
| E | —CH(CH$_3$)$_2$ | —S(O$_2$)— | | | —OCF$_3$ | —CH$_3$ | 489 (M + 1, 47), 506 (16) 511 [M + 23, (30)], 548 (13) |

TABLE 2-continued

Spectral Data for selected Compounds in Table 1

| Cmpd. | R¹ | L¹ | M¹—Y | M²—Z | Y | Z | MS |
|---|---|---|---|---|---|---|---|
| F | —CH(CH$_3$)$_2$ | —S(O$_2$)— | (Y-substituted phenyl) | (phenyl with Z) | —OCF$_3$ | F | 503 (M+1, 67), 504 (22.64), 525 (M+23, 100) |
| G | —CH(CH$_3$)$_2$ | —S(O$_2$)— | (Y-substituted phenyl) | (pyridyl) | —OCF$_3$ | H | 486 (M+1, 100), 508 [M+23, (35.08)] |
| H | —CH(CH$_3$)$_2$ | —S(O$_2$)— | (N-substituted indole) | (phenyl with Z) | H | F | 458 (M+1, 100), 183 (90) |
| I | —CH(CH$_3$)$_2$ | —S(O$_2$)— | (Y-substituted phenyl) | (pyrimidyl) | —OCF$_3$ | H | 487.1 (M+1, 100), 509 [M+23, (80)], 425 (75) |
| J | —CH(CH$_3$)$_2$ | —CH$_2$— | (N-substituted indole) | (phenyl with Z) | H | F | 406 (M+1, 80), 275 (100) |
| K | (cyclopropyl) | —S(O$_2$)— | (Y-substituted phenyl) | (phenyl with Z) | Cl | F | 451.1 (M+1, 100), 130.0 (60) |
| L | —CH(CH$_3$)$_2$ | —S(O$_2$)— | (N-substituted indole) | (pyridyl) | H | H | 441 (M+1, 100), 377 (10) |

TABLE 2-continued

Spectral Data for selected Compounds in Table 1

| Cmpd. | R$^1$ | L$^1$ | M$^1$—Y | M$^2$—Z | Y | Z | MS |
|---|---|---|---|---|---|---|---|
| M | —CH(CH$_3$)$_2$ | —S(O$_2$)— | (2,4-disubstituted phenyl) | (1,2-disubstituted phenyl with Z) | —N(CH$_3$)$_2$ | F | 462 (M + 1, 100), 484 [M + 23, (30)] |
| N | —CH(CH$_3$)$_2$ | —S(O$_2$)— | (2,3-dihydrobenzofuran, 4,5-disubstituted) | (2-substituted pyridine) | H | H | 444 (M + 1, 100) |
| O | —N(CH$_3$)$_2$ | —S(O$_2$)— | (2,4-disubstituted phenyl) | (2-substituted pyridine) | —CH(CH$_3$)$_2$ | H | 445 (M + 1, 100) |
| P | —CH(CH$_3$)$_2$ | —S(O$_2$)— | (2,4-disubstituted phenyl) | (2-substituted pyridine) | —N(CH$_3$)$_2$ | H | 445.1 (M + 1, 100), 431 (10) |
| Q | —CH(CH$_3$)$_2$ | —S(O$_2$)— | (2,4-disubstituted phenyl) | (2-substituted pyridine N-oxide) | —CH(CH$_3$)$_2$ | H | 460.1 (M + 1, 100), 482 (M + 23, (50)) |
| R | —CH(CH$_3$)$_2$ | —S(O$_2$)— | (2,4-disubstituted phenyl) | (1,2-disubstituted phenyl with Z) | —OH | F | 435 (M + 1, 100), 457 (M + 23 (10)) |
| S | —CH(CH$_3$)$_2$ | —S(O$_2$)— | (2,4-disubstituted phenyl) | (1,2-disubstituted phenyl with Z) | —OCH$_2$CH$_2$OCH$_3$ | F | 493 (M + 1, 100), 515 (M + 23 (10)) |

TABLE 2-continued

Spectral Data for selected Compounds in Table 1

| Cmpd. | R¹ | L¹ | M¹—Y | M²—Z | Y | Z | MS |
|---|---|---|---|---|---|---|---|
| T | —CH(CH₃)₂ | covalent bond | Y-phenyl | piperidine-N-Z | —CH(CH₃)₂ | —CH₃ | 464 [(M − HCl) + 1, 100] |
| U | —CH(CH₃)₂ | —S(O₂)— | Y-phenyl | pyridine | morpholine-N | H | 487 (M + 1, 100) |
| V | morpholine-N | —S(O₂)— | Y-phenyl | pyridine | —CH(CH₃)₂ | H | 487 (M + 1, 100) |
| W | cyclopropyl | —S(O₂)— | Y-phenyl | pyridine | —OCH₃ | H | 464 (M + 1, 100) |
| X | —CH(CH₃)₂ | —S(O₂)— | Y-phenyl-CHO | pyridine | —CH(CH₃)₂ | H | 472 (M + 1, 100), 486 (50), 504 (45) |
| Y | —CH(CH₃)₂ | —S(O₂)— | Y-phenyl-OH | pyridine | —CH(CH₃)₂ | H | 474 (M + 1, 100) |
| Z | cyclopropyl | —S(O₂)— | Y-phenyl | pyridine | imidazole-N | H | 466.1 (M + 1, 100), 488 (40) |

TABLE 2-continued

Spectral Data for selected Compounds in Table 1

| Cmpd. | R¹ | L¹ | M¹—Y | M²—Z | Y | Z | MS |
|---|---|---|---|---|---|---|---|
| AA | cyclopropylmethyl | —S(O₂)— | Y-phenyl | 2-pyridyl | HN-cyclopropyl | H | 455 (100), 477 (50), 346 (30), 232 (75), 200 (80) |
| AB | —CH(CH₃)₂ | —S(O₂)— | Y-phenyl | 2-pyridyl | —CN | H | 427.1 (M+1, 100), 253 (12), 149.0 (17) |
| AC | —CH(CH₃)₂ | —S(O₂)— | Y-phenyl | 2-pyridyl | methyl propanoate | H | 460 (M+1, 100) |
| AD | —CH(CH₃)₂ | —S(O₂)— | Y-phenyl | 2-pyridyl | —CF₃ | H | 470 (M+1, 50) 492 (50), 134 (30) |
| AE | —CH(CH₃)₂ | —S(O₂)— | oxanorbornene | phenyl-Z | H | F | 437 (M+1, 369, 277) |
| AF | —CH(CH₃)₂ | —S(O₂)— | Y-phenyl | phenyl-Z | —OCH₃ | F | 449 (M+1, 65), 471 (100), 159 (65) |
| AG | —CH(CH₃)₂ | —S(O₂)— | Y-phenyl | 2-pyridyl | —OCH₃ | H | 454.1 (M+1, 100), 432 (50) |

TABLE 2-continued

Spectral Data for selected Compounds in Table 1

| Cmpd. | R[1] | L[1] | M[1]—Y | M[2]—Z | Y | Z | MS |
|---|---|---|---|---|---|---|---|
| AH | cyclopropyl | —S(O$_2$)— | Y-phenyl(Z) | phenyl(Z) | —OCH$_3$ | F | 447.1 (M+1, 100), 329.1 (10) |
| AI | cyclopropyl | —S(O$_2$)— | Y-phenyl(Z) | pyridyl | cyclopropyl | H | 440.1 (M+1, 100), 246.0 (6), 185.0 (6) |
| AJ | —CH(CH$_3$)$_2$ | —S(O$_2$)— | Y-phenyl(Z) | pyridyl | —CH(CH$_3$)$_2$ | H | 444 (M+1) |
| AK | —CH(CH$_3$)$_2$ | —S(O$_2$)— | Y-phenyl(Z) | phenyl(Z) | —OCH(CH$_3$)$_2$ | F | 477 (M+1), 357 (10) |
| AL | —CH(CH$_3$)$_2$ | —S(O$_2$)— | Y-phenyl(Z) | pyridyl | —OCH(CH$_3$)$_2$ | H | 460.1 (M+1, 100), 418 (05) |
| AM | —OCH(CH$_3$)$_2$ | —S(O$_2$)— | Y-phenyl(Z) | pyridyl | —CH(CH$_3$)$_2$ | H | 460 (M+1, 100), 482 (M+23, (25)) |
| AN | —CH(CH$_3$)$_2$ | —S(O$_2$)— | Y-phenyl(Z) | Z-pyridyl | —OCH(CH$_3$)$_2$ | —C(O)OCH$_3$ | 518 (M+1, 100 540 (50), 248 (75), 210 (65) |

TABLE 2-continued

Spectral Data for selected Compounds in Table 1

| Cmpd. | $R^1$ | $L^1$ | $M^1$—Y | $M^2$—Z | Y | Z | MS |
|---|---|---|---|---|---|---|---|
| AO | —CH(CH$_3$)$_2$ | —S(O$_2$)— | (1-methylindol-2,3-diyl) | (2-Z-phenyl) | H | F | (472 (M + 1, 100), 376 (30) |
| AP | —CH(CH$_3$)$_2$ | —S(O$_2$)— | (1H-indol-2,3-diyl) | (pyridin-2-yl) | H | H | 441, (M + 1, 100) |
| AQ | —CH(CH$_3$)$_2$ | —S(O$_2$)— | (1-methylindol-2,3-diyl) | (pyridin-2-yl) | H | H | (455 (M + 1, 100) |
| AR | —CH(CH$_3$)$_2$ | —S(O$_2$)— | (Y-phenyl-diyl) | (thiophen-2-yl) | —CF$_3$ | H | 475.1 (M + 1, 100), 497 (M + 23, (45)), 459NL (35) |
| AS | —CH(CH$_3$)$_2$ | —S(O$_2$)— | (furan-2,3-diyl) | (pyridin-2-yl) | H | H | 392 (M + 1) |

It will be understood that various modifications may be made to the embodiments and examples disclosed herein. Therefore, the above description should not be construed as limiting, but merely as exemplifications of preferred embodiments. Those skilled in the art will envision various modifications within the scope and spirit of the claims appended hereto.

We claim:

1. A compound having the formula II,

II or a pharmaceutically acceptable salt thereof, wherein $R^1$, $L^1$, $M^1$, $M^2$, Y and Z are selected from the groups consisting of:

| $R^1$ | $L^1$ | $M^1$-Y |
|---|---|---|
| —CH(CH$_3$)$_2$ | —CH$_2$— |  |

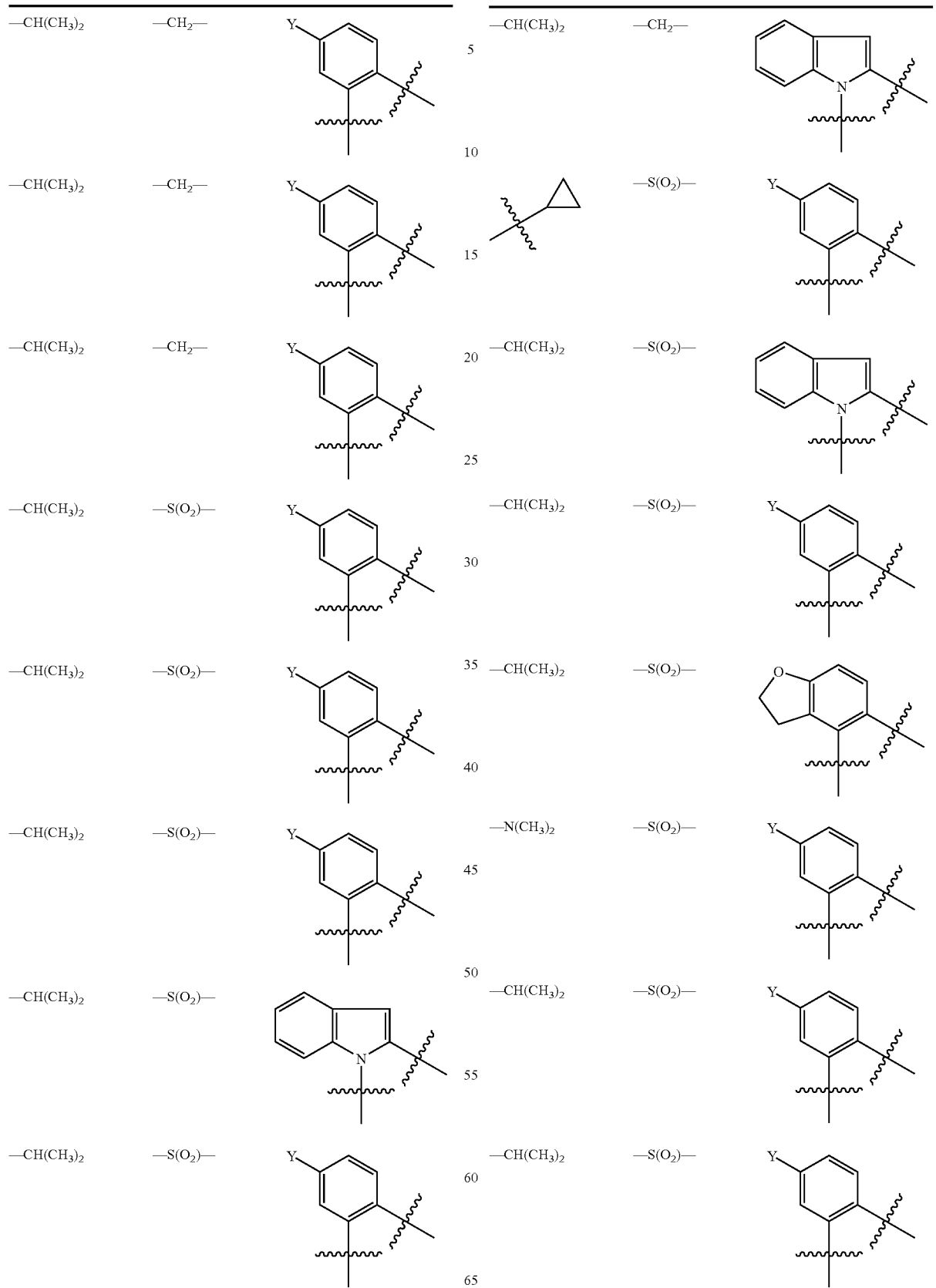

-continued
| | | |
|---|---|---|
| —CH(CH₃)₂ | —S(O₂)— | 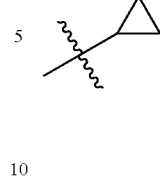 |
| —CH(CH₃)₂ | —S(O₂)— | 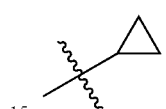 |
| —CH(CH₃)₂ | Covalent bond | Y phenyl |
| —CH(CH₃)₂ | —S(O₂)— | Y phenyl |
| 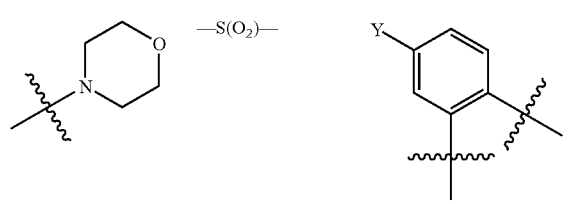 morpholine | —S(O₂)— | Y phenyl |
| 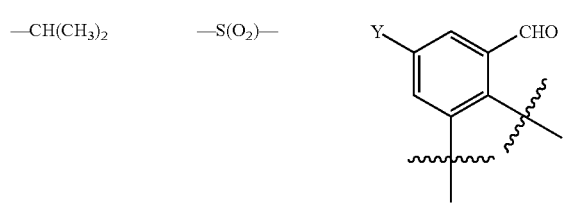 cyclopropyl | —S(O₂)— | Y phenyl |
| —CH(CH₃)₂ | —S(O₂)— | 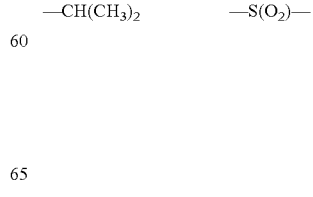 Y-phenyl-CHO |
| —CH(CH₃)₂ | —S(O₂)— | Y-phenyl-CH₂OH |
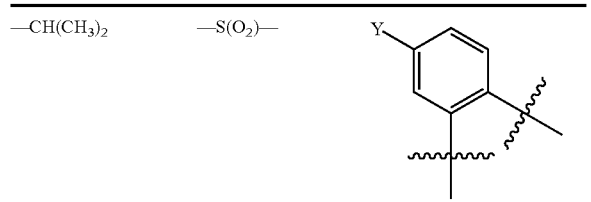
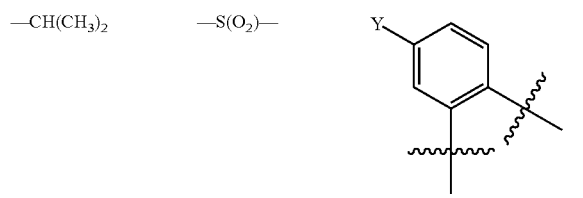
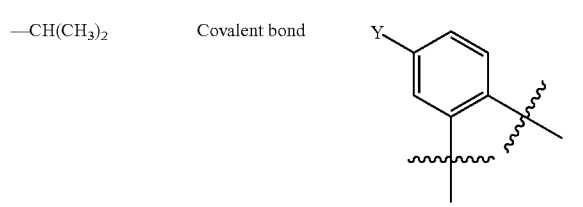
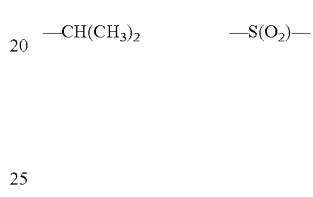
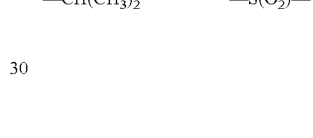
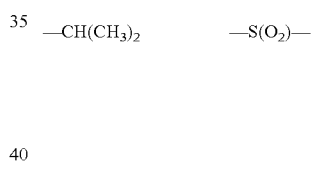
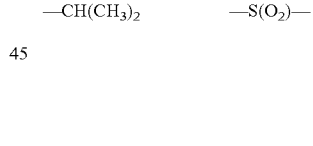
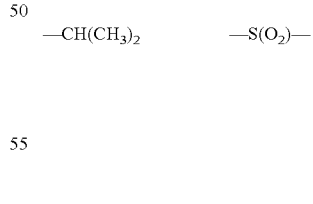
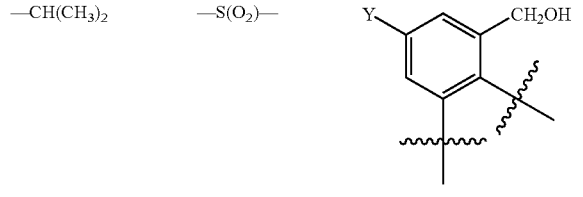
-continued
| | | |
|---|---|---|
| 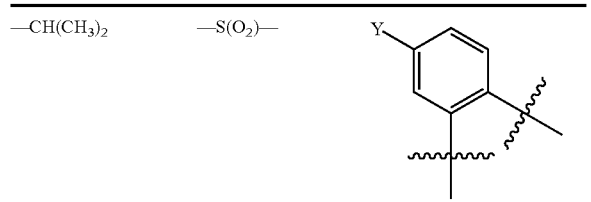 cyclopropyl | —S(O₂)— | 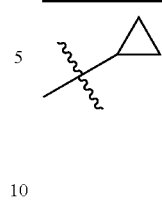 |
| 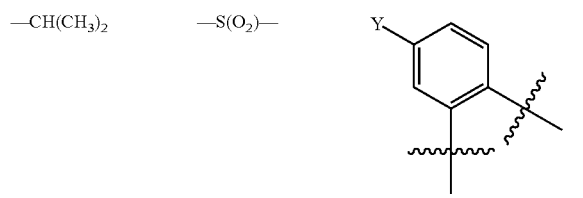 cyclopropyl | —S(O₂)— | 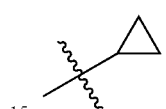 |
| —CH(CH₃)₂ | —S(O₂)— | Y phenyl |
| —CH(CH₃)₂ | —S(O₂)— | Y phenyl |
| —CH(CH₃)₂ | —S(O₂)— | Y phenyl |
| —CH(CH₃)₂ | —S(O₂)— | 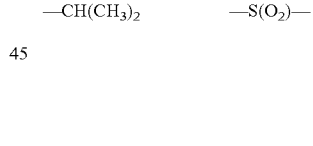 oxanorbornene |
| —CH(CH₃)₂ | —S(O₂)— | Y phenyl |
| —CH(CH₃)₂ | —S(O₂)— | Y phenyl |
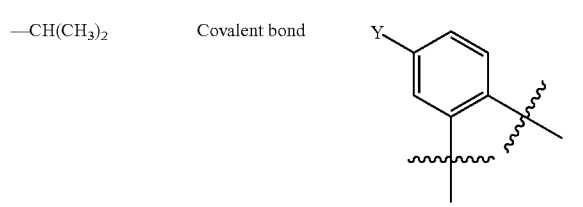
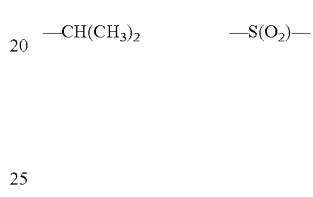
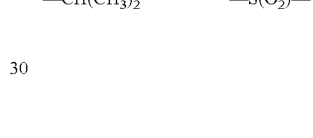
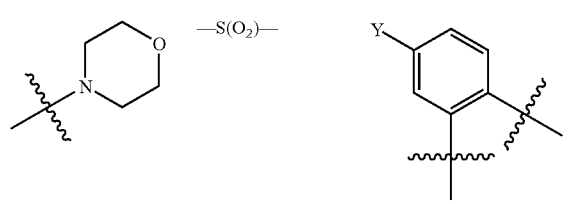
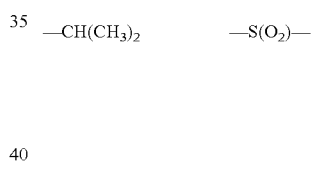
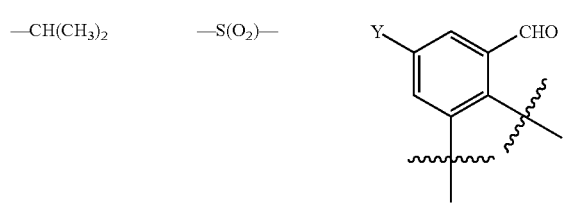
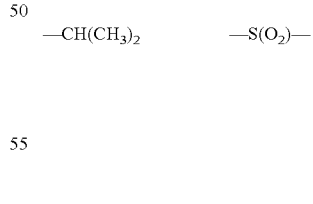
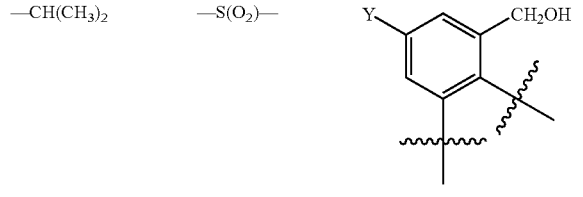
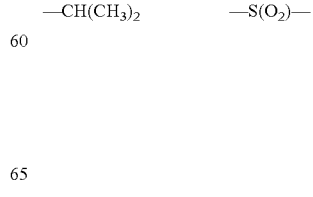

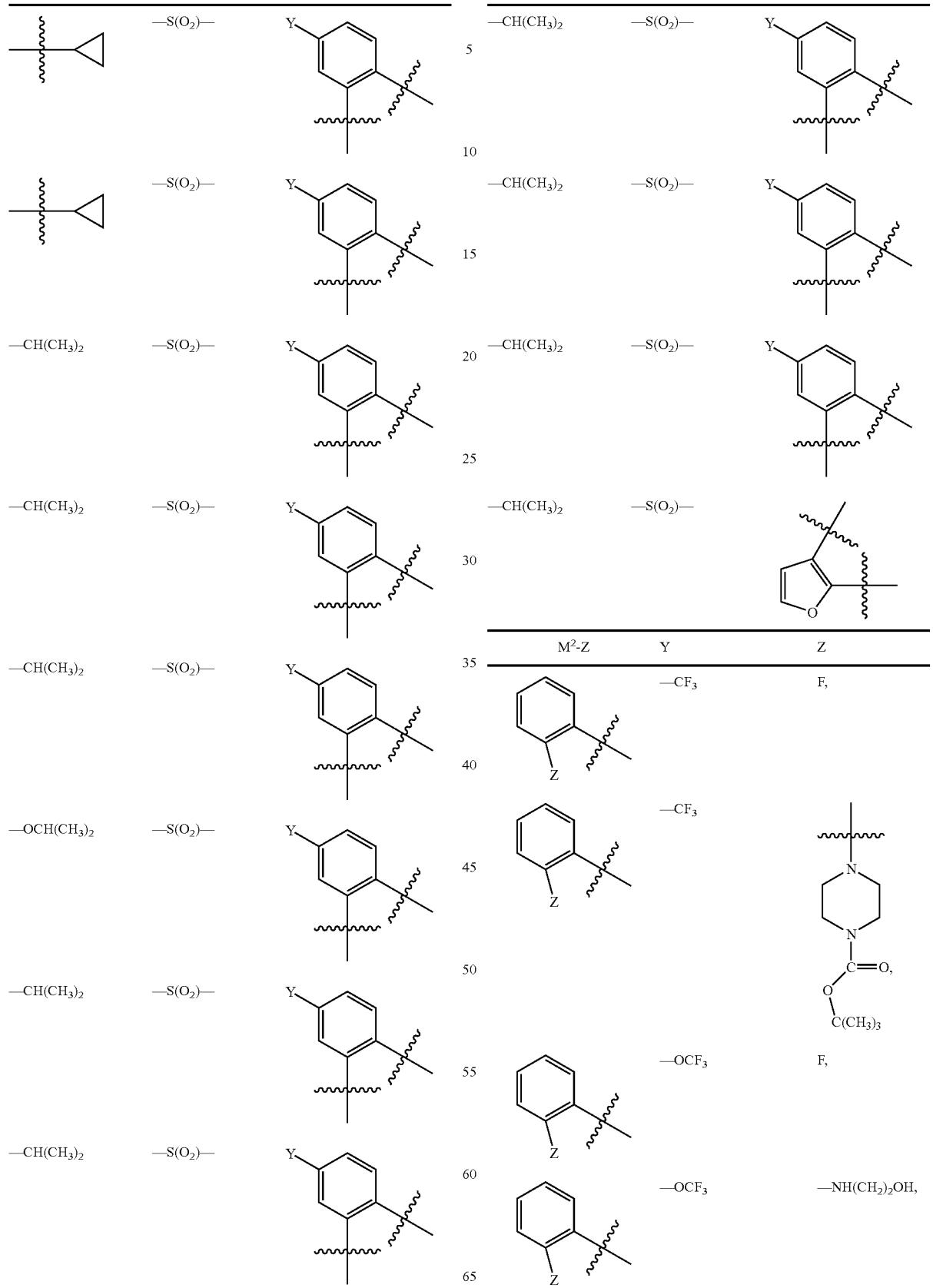

| Structure | R | R' |
|---|---|---|
| furan-Z | —OCF₃ | —CH₃, |
| phenyl-Z | —OCF₃ | F, |
| pyridyl | —OCF₃ | H, |
| phenyl-Z | H | F, |
| pyrimidinyl | —OCF₃ | H, |
| phenyl-Z | H | F, |
| phenyl-Z | Cl | F, |
| pyridyl | H | H, |
| phenyl-Z | N(CH₂)₂ | F, |
| pyridyl | H | H, |

| Structure | R | R' |
|---|---|---|
| pyridyl | —CH(CH₃)₂ | H, |
| pyridyl | —N(CH₃)₂ | H, |
| pyridyl N-oxide | —CH(CH₃)₂ | H, |
| phenyl-Z | OH | F, |
| phenyl-Z | —OCH₂CH₂OCH₃ | F, |
| piperidinyl-Z | —CH(CH₃)₂ | —CH₃, |
| pyridyl | morpholinyl | H, |
| pyridyl | —CH(CH₃)₂ | H, |
| pyridyl | —OCH₃ | H, |

| | | |
|---|---|---|
| 2-pyridyl | —CH(CH₃)₂ | H, |
| 2-pyridyl | —CH(CH₃)₂ | H, |
| 2-pyridyl | imidazolyl | H, |
| 2-pyridyl | N-cyclopropylamino (quaternary C) | H, |
| 2-pyridyl | —CN | H, |
| 2-pyridyl | —C(CH₃)₂C(O)OCH₃ | H, |
| 2-pyridyl | —CF₃ | H, |
| 2-Z-phenyl | H | F, |
| 2-Z-phenyl | —OCF₃ | F, |
| 2-pyridyl | —OCH₃ | H, |
| 2-Z-phenyl | —OCH₃ | F, |
| 2-pyridyl | cyclopropyl | H, |
| 2-pyridyl | —CH(CH₃)₂ | H, |
| 2-Z-phenyl | —OCH(CH₃)₂ | F, |
| 2-pyridyl | —OCH(CH₃)₂ | H, |
| 2-pyridyl | —CH(CH₃)₂ | H, |
| 5-Z-2-pyridyl | —OCH(CH₃)₂ | —COOCH₃, |
| 2-Z-phenyl | H | F, |
| 2-Z-phenyl | H | H, |
| 2-Z-phenyl | H | H, |
| 2-thienyl | —CF₃ | H, and |

-continued

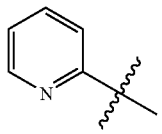

2. A compound having the formula III:

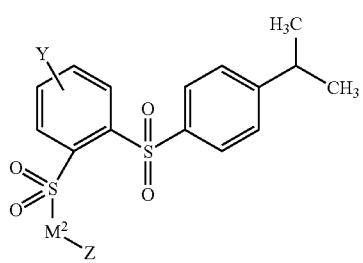

or a pharmaceutically acceptable salt thereof, wherein
Y is selected from the group consisting of hydrogen, alkoxy, alkyl, —CF$_3$, cycloalkyl, halogen, —OCF$_3$ and —OH;
Z is selected from the group consisting of hydrogen, alkyl, —CF$_3$, halogen, —N(R$^2$)$_2$, —OCF$_3$ and —OH; and
M$^2$ is aryl or heteroaryl.

3. The compound having the formula:

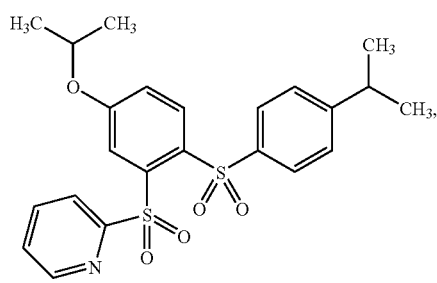

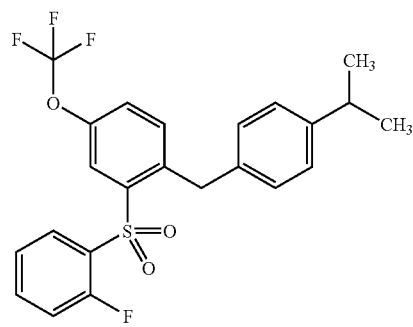

-continued

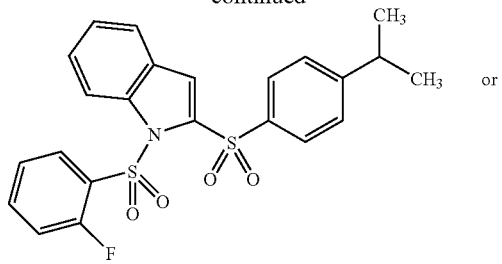

or

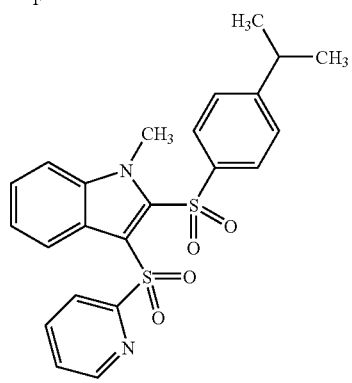

or a pharmaceutically acceptable salt thereof.

4. A pharmaceutical composition comprising at least one compound according to claim 1, or a pharmaceutically acceptable salt thereof, and a pharmaceutically acceptable carrier.

5. A pharmaceutical composition comprising an effective amount of at least one compound according to claim 2, or a pharmaceutically acceptable salt thereof, and a pharmaceutically acceptable carrier.

6. A process for making a pharmaceutical composition comprising combining at least one compound of claim 1, or a pharmaceutically acceptable salt thereof, and at least one pharmaceutically acceptable carrier.

7. A process for making a pharmaceutical composition comprising combining at least one compound of claim 2, or a pharmaceutically acceptable salt thereof, and at least one pharmaceutically acceptable carrier.

8. A method of treating inflammatory diseases, immunomodulatory diseases, or respiratory diseases comprising administering to a mammal in need of such treatment an effective amount of at least one compound according to claim 1, or a pharmaceutically acceptable salt thereof.

9. A method of treating inflammatory diseases, immunomodulatory diseases, or respiratory diseases comprising administering to a mammal in need of such treatment an effective amount of at least one compound according to claim 2, or a pharmaceutically acceptable salt thereof.

10. A method of treating rheumatoid arthritis, systemic lupus erythematosus, multiple sclerosis, glaucoma, diabetes, sepsis, shock, sarcoidosis, idiopathic pulmonary fibrosis, bronchopulmonary dysplasia, retinal disease, scieroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, Crohn's disease, inflammatory bowel disease, reversible airway obstruction, adult respiratory distress syndrome, asthma, chronic obstructive pulmonary disease (COPD) or bronchitis comprising administering to a mammal in need of such treatment an effective amount of at least one compound according to claim 1 or a pharmaceutically acceptable salt thereof.

11. A method of treating rheumatoid arthritis, systemic lupus erythematosus, multiple sclerosis, glaucoma, diabetes, sepsis, shock, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, Crohn's disease, inflammatory bowel disease, reversible airway obstruction, adult respiratory distress syndrome, asthma, chronic obstructive pulmonary disease (COPD) or bronchitis comprising administering to a mammal in need of such treatment an effective amount of at least one compound according to claim 2 or a pharmaceutically acceptable salt thereof.

12. The method of claim 8 wherein the condition or disease treated is selected from rheumatoid arthritis, multiple sclerosis, seasonal allergic rhinitis, psoriasis, transplant rejection and chronic obstructive pulmonary disease.

13. The method of claim 9 wherein the condition or disease treated is selected from rheumatoid arthritis, multiple sclerosis, seasonal allergic rhinitis, psoriasis, transplant rejection and chronic obstructive pulmonary disease.

14. A process for making a pharmaceutical composition comprising combining at least one compound of claim 1, or a pharmaceutically acceptable salt thereof, and at least one pharmaceutically acceptable carrier.

15. A process for making a pharmaceutical composition comprising combining at least one compound of claim 2, or a pharmaceutically acceptable salt thereof, and at least one pharmaceutically acceptable carrier.

16. A method of treating rheumatoid arthritis comprising administering to a mammal in need thereof an effective amount of at least one compound of claim 1, or a pharmaceutically acceptable salt thereof, in combination with at least one compound selected from the class consisting of a COX-2 inhibitor, a COX-1 inhibitor, an immunosuppressive, a steroid, an anti-TNF-α compound or other classes of compounds indicated for the treatment of rheumatoid arthritis.

17. A method of treating rheumatoid arthritis comprising administering to a mammal in need thereof an effective amount of at least one compound of claim 2, or a pharmaceutically acceptable salt thereof, in combination with at least one compound selected from the class consisting of a COX-2 inhibitor, a COX-1 inhibitor, an immunosuppressive, a steroid, an anti-TNF-α compound or other classes of compounds indicated for the treatment of rheumatoid arthritis.

18. The method of claim 16 wherein the COX-2 inhibitor is Celebrex or Vioxx, the COX-1 inhibitor is Feldene, the immunosuppressive is methotrexate, leflunomide, sulfasalazine, or cyclosporin, the steroid is β-methasone and the anti-TNF-α compound is Enbrel or Remicade.

19. The method of claim 17 wherein the COX-2 inhibitor is Celebrex or Vioxx, the COX-1 inhibitor is Feldene, the immunosuppressive is methotrexate, leflunomide, sulfasalazine, or cyclosporin, the steroid is β-methasone and the anti-TNF-α compound is Enbrel or Remicade.

20. A composition for treating rheumatoid arthritis which comprises a compound selected from the class consisting of a COX-2 inhibitor, a COX-1 inhibitor, an immunosuppressive, a steroid, an anti-TNF-α compound or other classes of compounds indicated for the treatment of rheumatoid arthritis and an effective amount of at least one compound of claim 1, or a pharmaceutically acceptable salt thereof.

21. A composition for treating rheumatoid arthritis which comprises a compound selected from the class consisting of a COX-2 inhibitor, a COX-1 inhibitor, an immunosuppressive, a steroid, an anti-TNF-α compound or other classes of compounds indicated for the treatment of rheumatoid arthritis and an effective amount of at least one compound of claim 2, or a pharmaceutically acceptable salt thereof.

22. The composition of claim 20 wherein the COX-2 inhibitor is Celebrex or Vioxx, the COX-1 inhibitor is Feldene, the immunosuppressive is methotrexate, leflunomide, sulfasalazine, or cyclosporin, the steroid is β-methasone and the anti-TNF-α compound is Enbrel or Remicade.

23. The composition of claim 21 wherein the COX-2 inhibitor is Celebrex or Vioxx, the COX-1 inhibitor is Feldene, the immunosuppressive is methotrexate, leflunomide, sulfasalazine, or cyclosporin, the steroid is β-methasone and the anti-TNF-α compound is Enbrel or Remicade.

24. A method of treating multiple sclerosis comprising administering to a mammal in need thereof an effective amount of at least one compound of claim 1, or a pharmaceutically acceptable salt thereof, in combination with an effective amount of a compound selected from Avonex, Betaseron, Copaxone or other compounds indicated for the treatment of multiple sclerosis.

25. A method of treating multiple sclerosis comprising administering to a mammal in need thereof an effective amount of at least one compound of claim 2, or a pharmaceutically acceptable salt thereof, in combination with an effective amount of a compound selected from Avonex, Betaseron, Copaxone or other compounds indicated for the treatment of multiple sclerosis.

26. A composition for treating multiple sclerosis which comprises a compound selected from Avonex, Betaseron, Copaxone or other compounds indicated for the treatment of multiple sclerosis and an effective amount of at least one compound of claim 1, or a pharmaceutically acceptable salt thereof.

27. A composition for treating multiple sclerosis which comprises a compound selected from Avonex, Betaseron, Copaxone or other compounds indicated for the treatment of multiple sclerosis and an effective amount of at least one compound of claim 2, or a pharmaceutically acceptable salt thereof.

28. A method of treating psoriasis comprising administering to a mammal in need thereof an effective amount of at least one compound as defined in claim 1, or a pharmaceutically acceptable salt thereof, in combination with a compound selected from the class consisting of an immunosuppressive, a steroid, an anti-TNF-α compound or other classes of compounds indicated for the treatment of psoriasis.

29. A method of treating psoriasis comprising administering to a mammal in need thereof an effective amount of at least one compound as defined in claim 2, or a pharmaceutically acceptable salt thereof, in combination with a compound selected from the class consisting of an immunosuppressive, a steroid, an anti-TNF-α compound or other classes of compounds indicated for the treatment of psoriasis.

30. The method of claim 28 wherein the immunosuppressive is methotrexate, leflunomide, sulfasalazine or cyclosporin, the steroid is β-methasone and the anti-TNF-α compound is Enbrel or Remicade.

31. The method of claim 29 wherein the immunosuppressive is methotrexate, leflunomide, sulfasalazine or cyclosporin, the steroid is β-methasone and the anti-TNF-α compound is Enbrel or Remicade.

32. A composition for treating psoriasis which comprises a compound selected from the class consisting of an immunosuppressive, a steroid, an anti-TNF-α compound or other classes of compounds indicated for the treatment of psoriasis and an effective amount of at least one compound of claim 1, or a pharmaceutically acceptable salt thereof.

33. A composition for treating psoriasis which comprises a compound selected from the class consisting of an immunosuppressive, a steroid, an anti-TNF-α compound or other classes of compounds indicated for the treatment of psoriasis and an effective amount of at least one compound of claim 2, or a pharmaceutically acceptable salt thereof.

34. The composition of claim 32 wherein the immunosuppressive is methotrexate, leflunomide, sulfasalazine or cyclosporin, the steroid is β-methasone and the anti-TNF-α compound is Enbrel or Remicade.

35. The composition of claim 33 wherein the immunosuppressive is methotrexate, leflunomide, sulfasalazine or cyclosporin, the steroid is β-methasone and the anti-TNF-α compound is Enbrel or Remicade.

36. A method of treating seasonal allergic rhinitis and/or asthma comprising an effective amount of at least one compound of claim 1, or a pharmaceutically acceptable salt thereof, in combination with at least one H1 antagonist.

37. A method of treating seasonal allergic rhinitis and/or asthma comprising an effective amount of at least one compound of claim 2, or a pharmaceutically acceptable salt thereof, in combination with at least one H1 antagonist.

38. A composition for treating seasonal allergic rhinitis and/or asthma which comprises an effective amount of at least one H1 antagonist and an effective amount of at least one compound of claim 1, or a pharmaceutically acceptable salt thereof.

39. A composition for treating seasonal allergic rhinitis and/or asthma which comprises an effective amount of at least one H1 antagonist and an effective amount of at least one compound of claim 2, or a pharmaceutically acceptable salt thereof.

40. The composition of claim 38 wherein the H1 antagonist is selected from Claritin, Clarinex, Zyrtec and Allegra.

41. The composition of claim 39 wherein the H1 antagonist is selected from Claritin, Clarinex, Zyrtec and Allegra.

42. A pharmaceutical composition comprising at least one compound according to claim 3, or a pharmaceutically acceptable salt thereof, and a pharmaceutically acceptable carrier.

43. A process for making a pharmaceutical composition comprising combining at least one compound of claim 3, or a pharmaceutically acceptable salt thereof, and at least one pharmaceutically acceptable carrier.

44. A method of treating inflammatory diseases, immunomodulatory diseases, or respiratory diseases comprising administering to a mammal in need of such treatment an effective amount of at least one compound according to claim 3, or a pharmaceutically acceptable salt thereof.

\* \* \* \* \*

UNITED STATES PATENT AND TRADEMARK OFFICE
CERTIFICATE OF CORRECTION

| | | |
|---|---|---|
| PATENT NO. | : 7,642,272 B2 | Page 1 of 1 |
| APPLICATION NO. | : 10/803577 | |
| DATED | : January 5, 2010 | |
| INVENTOR(S) | : Bandarpalle B. Shankar et al. | |

It is certified that error appears in the above-identified patent and that said Letters Patent is hereby corrected as shown below:

On the Title page,

Item [*] Notice:   Subject to any disclaimer, the term of this patent is extended or adjusted under 35 U.S.C. 154(b) by 164 days.

Delete the phrase "by 164 days" and insert -- by 291 days --

Signed and Sealed this

Tenth Day of August, 2010

David J. Kappos
*Director of the United States Patent and Trademark Office*